US012616810B2

(12) United States Patent
LaTorraca et al.

(10) Patent No.: US 12,616,810 B2
(45) Date of Patent: May 5, 2026

(54) ACCURATE PRESSURE MEASUREMENT WITH NON-INVASIVE VENTILATION NASAL PILLOWS

(71) Applicant: HILL-ROM SERVICES PTE. LTD., Ot (SG)

(72) Inventors: Gary John LaTorraca, Batesville, IN (US); Tom Westfall, Batesville, IN (US); Simon Jung, Batesville, IN (US)

(73) Assignee: HILL-ROM SERVICES PTE.LTD., Ot (SG)

( * ) Notice: Subject to any disclaimer, the term of this patent is extended or adjusted under 35 U.S.C. 154(b) by 989 days.

(21) Appl. No.: 17/712,861

(22) Filed: Apr. 4, 2022

(65) Prior Publication Data

US 2022/0339378 A1     Oct. 27, 2022

Related U.S. Application Data

(60) Provisional application No. 63/310,223, filed on Feb. 15, 2022, provisional application No. 63/177,533, filed on Apr. 21, 2021.

(51) Int. Cl.
*A61M 16/00* (2006.01)
*A61M 16/06* (2006.01)
(52) U.S. Cl.
CPC .... *A61M 16/0012* (2014.02); *A61M 16/0003* (2014.02); *A61M 16/024* (2017.08); *A61M 16/0666* (2013.01); *A61M 2016/0027* (2013.01)
(58) Field of Classification Search
CPC .......... A61M 16/0012; A61M 16/0003; A61M 16/0666; A61M 16/0858; A61M 16/127; A61M 16/0672; A61M 2205/3327
See application file for complete search history.

(56) References Cited

U.S. PATENT DOCUMENTS

| | | | | |
|---|---|---|---|---|
| 3,400,714 A | | 9/1968 | Sheridan | |
| 5,099,836 A | * | 3/1992 | Rowland | A61M 16/0051 |
| | | | | 128/207.18 |

(Continued)

FOREIGN PATENT DOCUMENTS

| | | |
|---|---|---|
| CN | 102762250 A | 10/2012 |
| CN | 109675155 A | 4/2019 |

(Continued)

OTHER PUBLICATIONS

English Translation of Ao, 2020. (Year: 2025).*

(Continued)

*Primary Examiner* — Kendra D Carter
*Assistant Examiner* — Maap Ellabib
(74) *Attorney, Agent, or Firm* — Stetina Garred Brucker & Newboles

(57)     ABSTRACT

A patient ventilation interface has a throat body defining a venturi throat that is open to ambient air, a nasal pillow disposed around the venturi throat to define a plenum between the venturi throat and the nasal pillow, a jet nozzle arranged to output ventilation gas into the venturi throat, and a pressure sensing tube having a pressure sensing port positioned to be in fluid communication with the plenum. The nasal pillow may be an integral part of the throat body. An expected error in the sensed patient airway pressure $P_{sense}$ may be corrected by applying a correction factor $P_{delta}$ indexed by the sensed patient airway pressure $P_{sense}$ and a jet nozzle flow $V'_n$ of the jet nozzle. Delivery of the ventilation gas output by the jet nozzle may be controlled in response to the corrected patient airway pressure.

24 Claims, 11 Drawing Sheets

(56) References Cited

U.S. PATENT DOCUMENTS

| | | | |
|---|---|---|---|
| 7,987,850 | B2 | 8/2011 | Zollinger et al. |
| 8,100,125 | B2 | 1/2012 | Duquette et al. |
| 8,371,304 | B2 | 2/2013 | Duquette et al. |
| 9,199,053 | B1 * | 12/2015 | Allum ................. A61M 16/085 |
| 9,962,512 | B2 | 5/2018 | Cipollone et al. |
| 10,046,133 | B2 | 8/2018 | Kapust et al. |
| 10,080,521 | B2 | 9/2018 | Parrish |
| 10,265,486 | B2 | 4/2019 | Allum et al. |
| 10,265,493 | B2 | 4/2019 | Heatherington et al. |
| 10,376,666 | B2 | 8/2019 | Mcauley et al. |
| 10,384,028 | B2 | 8/2019 | Allum et al. |
| 10,478,580 | B2 | 11/2019 | Gulliver et al. |
| 10,537,694 | B2 | 1/2020 | Mcauley et al. |
| 10,625,035 | B2 | 4/2020 | Fleming et al. |
| 10,709,864 | B2 | 7/2020 | Kapust et al. |
| 10,751,501 | B2 | 8/2020 | Nussbaum et al. |
| 10,792,449 | B2 | 10/2020 | Brambilla et al. |
| 11,191,915 | B2 | 12/2021 | Ahmad |
| 11,291,785 | B2 | 4/2022 | Shahar et al. |
| 11,291,791 | B2 | 4/2022 | Devries et al. |
| 2008/0223375 | A1 | 9/2008 | Cortez et al. |
| 2010/0252040 | A1 | 10/2010 | Kapust et al. |
| 2013/0092165 | A1 | 4/2013 | Wondka |
| 2015/0209533 | A1 | 7/2015 | Boussignac |
| 2016/0193438 | A1 * | 7/2016 | White ............... A61M 16/1005 128/204.23 |
| 2017/0000965 | A1 * | 1/2017 | Cortez, Jr. ........ A61M 16/0666 |
| 2018/0200464 | A1 | 7/2018 | Borrello |
| 2019/0232000 | A1 * | 8/2019 | Allum ............... A61M 16/0672 |
| 2019/0240438 | A1 | 8/2019 | Stenzler et al. |
| 2020/0101252 | A1 | 4/2020 | Oddo |
| 2021/0016029 | A1 | 1/2021 | Kuo et al. |
| 2021/0046271 | A1 | 2/2021 | Sobel et al. |
| 2021/0113747 | A1 | 4/2021 | Bullock et al. |
| 2021/0154427 | A1 | 5/2021 | Poon et al. |
| 2022/0126052 | A1 * | 4/2022 | Fitch ................. A61M 16/0858 |
| 2022/0148701 | A1 | 5/2022 | Cipollone et al. |

FOREIGN PATENT DOCUMENTS

| | | | | |
|---|---|---|---|---|
| FR | 2827778 | A1 | 1/2003 | |
| WO | WO-2015125080 | A1 * | 8/2015 | ........ A61M 16/0875 |
| WO | WO-2020118871 | A1 * | 6/2020 | ............. G05D 27/00 |
| WO | 2020154700 | A1 | 7/2020 | |

OTHER PUBLICATIONS

Extended European Search Report for EP Application No. 22168989. 6; mailed Sep. 9, 2022.

First Chinese Office Action for Chinese Application No. 202210427398. 1; mailed Aug. 30, 2025.

* cited by examiner

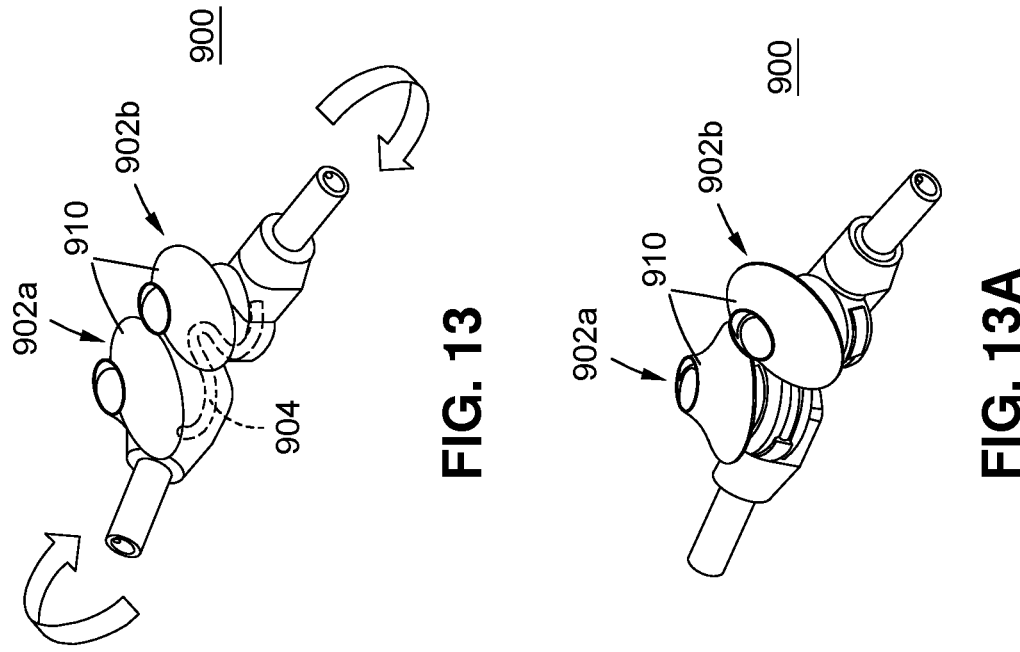
FIG. 13
FIG. 13A
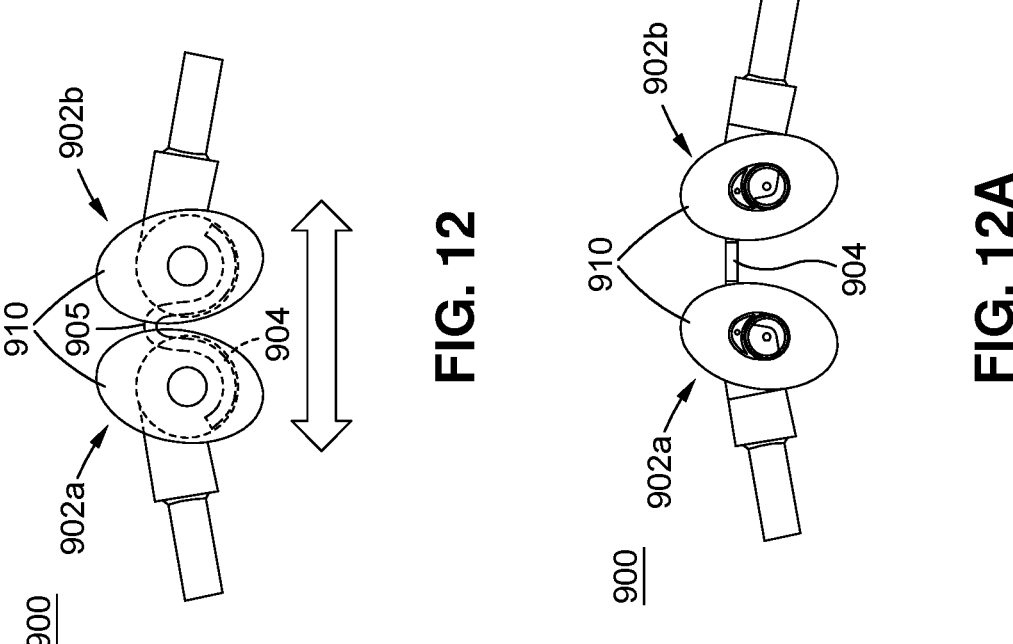
FIG. 12
FIG. 12A

ACCURATE PRESSURE MEASUREMENT WITH NON-INVASIVE VENTILATION NASAL PILLOWS

CROSS-REFERENCE TO RELATED APPLICATIONS

The present application claims priority to U.S. Provisional Application Ser. No. 63/177,533, filed Apr. 21, 2021, and U.S. Provisional Application Ser. No. 63/310,223, filed Feb. 15, 2022, the disclosures of both of which are incorporated by reference herein.

STATEMENT RE: FEDERALLY SPONSORED RESEARCH/DEVELOPMENT

Not Applicable

BACKGROUND

1. Technical Field

The present disclosure relates generally to devices and methods for the administration of non-invasive ventilation (NIV) therapy and, more particularly, to an improved nasal pillows patient ventilation interface having integrated pressure sensing functionality adapted to be less susceptible to error attributable to increases in flow velocity.

2. Description of the Related Art

For administering non-invasive ventilation (NIV) to patients having chronic obstructive pulmonary disease (COPD) or other respiratory conditions, patient comfort may best be achieved with a physically small nasal pillows interface. Unlike larger assemblies such as nasal masks or full-face masks, nasal pillows are primarily confined to the space within and immediately below the patient's nares or nostrils and do not significantly encumber the patient's face. By the same token, given that knowledge of the actual pressure in the patient's airway is important for proper NIV function as well as for compliance with international standards for medical devices, it would be beneficial for pressure sensing to be integrated into the confines of nasal pillows in order to minimize the overall encumbrance of the interface. However, nasal pillows present significant hurdles when it comes to integrating pressure sensing functionality. In general, due to Bernoulli's principle, sensing pressure in a region where air is flowing is susceptible to error as flow velocity increases. The problem becomes profound when accurate pressure measurement is attempted within the small volume described by nasal pillows. The present disclosure contemplates various systems and methods for overcoming the above drawbacks accompanying the related art.

BRIEF SUMMARY

One aspect of the embodiments of the present disclosure is a patient ventilation interface, such as a nasal pillows interface. The patient ventilation interface may comprise a throat body defining a venturi throat that is open to ambient air, a nasal pillow disposed around the venturi throat to define a plenum between the venturi throat and the nasal pillow, a jet nozzle arranged to output ventilation gas into the venturi throat, and a pressure sensing tube having a pressure sensing port positioned to be in fluid communication with the plenum.

The nasal pillow may be an integral part of the throat body. The plenum may have a crescent-shaped cross-section. The venturi throat may taper outwardly away from the jet nozzle. The throat body may have greater rigidity than the nasal pillow. An outer surface of the throat body may be splined. The patient ventilation interface may comprise a ventilation gas tube terminating in the jet nozzle. At least a part of the pressure sensing tube may be disposed within the ventilation gas tube. The pressure sensing tube may extend from the ventilation gas tube into the throat body to position the pressure sensing port in fluid communication with the plenum. The pressure sensing port of the pressure sensing tube may be in fluid communication with the plenum via a pressure sensing passage defined by the throat body.

Another aspect of the embodiments of the present disclosure is a patient ventilation interface which may comprise a throat body defining a venturi throat that is open to ambient air, a nasal pillow disposed around the throat body to define an annular plenum between the throat body and the nasal pillow, a jet nozzle arranged to output ventilation gas into the venturi throat, and a pressure sensing tube having a pressure sensing port positioned to be in fluid communication with the annular plenum.

The throat body may have greater rigidity than the nasal pillow. An outer surface of the throat body may be splined. The patient ventilation interface may comprise a ventilation gas tube terminating in the jet nozzle. At least a part of the pressure sensing tube may be disposed within the ventilation gas tube. The pressure sensing tube may extend from the ventilation gas tube into the nasal pillow to position the pressure sensing port in fluid communication with the annular plenum. The pressure sensing port of the pressure sensing tube may be in fluid communication with the annular plenum via a pressure sensing passage defined by the nasal pillow.

Another aspect of the embodiments of the present disclosure is a patient ventilation interface which may comprise a nasal pillow body defining a venturi throat that is open to ambient air and having a nasal pillow portion disposed around the venturi throat to define a plenum within the nasal pillow body and outside the venturi throat. The patient ventilation interface may further comprise a jet nozzle arranged to output ventilation gas into the venturi throat and a pressure sensing tube having a pressure sensing port positioned to be in fluid communication with the plenum.

The plenum may have a crescent-shaped cross-section. The venturi throat may taper outwardly away from the jet nozzle. The patient ventilation interface may comprise a ventilation gas tube terminating in the jet nozzle. At least a part of the pressure sensing tube may be disposed within the ventilation gas tube. The pressure sensing tube may extend from the ventilation gas tube into the nasal pillow body to position the pressure sensing port in fluid communication with the plenum. The pressure sensing port of the pressure sensing tube may be in fluid communication with the plenum via a pressure sensing passage defined by the nasal pillow body.

Any of the above patient ventilation interfaces may comprise an entry piece defining a venturi inlet that is in fluid communication with the venturi throat. The jet nozzle may be arranged to output the ventilation gas into the venturi throat via the venturi inlet. The entry piece may define one or more entrainment openings by which the venturi throat is open to ambient air. The jet nozzle may be arranged to output the ventilation gas into the venturi inlet via an entrainment opening from among the one or more entrainment openings. The venturi inlet may flare outward relative to the venturi throat.

Another aspect of the embodiments of the present disclosure is a non-invasive ventilation system. The non-invasive ventilation system may comprise any of the above patient ventilation interfaces and a pressure sensor fluidly coupled to the pressure sensing tube.

The non-invasive ventilation system may comprise a controller programmed to control delivery of the ventilation gas output by the jet nozzle in response to a patient airway pressure $P_{sense}$ sensed by the pressure sensor. The controller may be programmed to correct for an expected error in the sensed patient airway pressure $P_{sense}$. The controller may be programmed to correct for the expected error by applying a correction factor $P_{delta}$ indexed by the sensed patient airway pressure $P_{sense}$. The correction factor $P_{delta}$ may be further indexed by a jet nozzle flow $V'_n$ of the jet nozzle.

The non-invasive ventilation system may comprise a non-transitory program storage medium on which are stored instructions, executable by a processor or programmable circuit, to correct for an expected error in the sensed patient airway pressure $P_{sense}$. The instructions may be executable by a processor or programmable circuit to correct for the expected error by applying a correction factor $P_{delta}$ indexed by the sensed patient airway pressure $P_{sense}$. The correction factor $P_{delta}$ may be further indexed by a jet nozzle flow $V'_n$ of the jet nozzle.

Another aspect of the embodiments of the present disclosure is a method of correcting a sensed patient airway pressure $P_{sense}$ in a patient ventilation interface. The method may comprise providing a patient ventilation interface including a throat body defining a venturi throat that is open to ambient air, a nasal pillow disposed around the venturi throat to define a plenum between the venturi throat and the nasal pillow, and a jet nozzle arranged to output ventilation gas into the venturi throat, sensing a patient airway pressure $P_{sense}$ in a pressure sensing tube having a pressure sensing port positioned to be in fluid communication with the plenum, and correcting for an expected error in the sensed patient airway pressure $P_{sense}$ by applying a correction factor $P_{delta}$ indexed by the sensed patient airway pressure $P_{sense}$. The correction factor $P_{delta}$ may be further indexed by a jet nozzle flow $V'_n$ of the jet nozzle.

The nasal pillow may be an integral part of the throat body.

Another aspect of the embodiments of the present disclosure is a method of non-invasive ventilation. The method may comprise providing a patient ventilation interface including a throat body defining a venturi throat that is open to ambient air, a nasal pillow disposed around the venturi throat to define a plenum between the venturi throat and the nasal pillow, and a jet nozzle arranged to output ventilation gas into the venturi throat, sensing a patient airway pressure $P_{sense}$ in a pressure sensing tube having a pressure sensing port positioned to be in fluid communication with the plenum, and controlling delivery of the ventilation gas output by the jet nozzle in response to a patient airway pressure $P_{sense}$ sensed by the pressure sensor.

The nasal pillow may be an integral part of the throat body.

Another aspect of the embodiments of the present disclosure is a method of correcting a sensed patient airway pressure $P_{sense}$ in a patient ventilation interface. The method may comprise providing a patient ventilation interface including a throat body defining a venturi throat that is open to ambient air, a nasal pillow disposed around the throat body to define an annular plenum between the throat body and the nasal pillow, and a jet nozzle arranged to output ventilation gas into the venturi throat. The method may include sensing a patient airway pressure $P_{sense}$ in a pressure sensing tube having a pressure sensing port positioned to be in fluid communication with the annular plenum. The method may include correcting for an expected error in the sensed patient airway pressure $P_{sense}$ by applying a correction factor $P_{delta}$ indexed by the sensed patient airway pressure $P_{sense}$. The correction factor $P_{delta}$ may be further indexed by a jet nozzle flow $V'_n$ of the jet nozzle.

Another aspect of the embodiments of the present disclosure is a method of non-invasive ventilation. The method may comprise providing a patient ventilation interface including a throat body defining a venturi throat that is open to ambient air, a nasal pillow disposed around the throat body to define an annular plenum between the throat body and the nasal pillow, and a jet nozzle arranged to output ventilation gas into the venturi throat. The method may comprise sensing a patient airway pressure $P_{sense}$ in a pressure sensing tube having a pressure sensing port positioned to be in fluid communication with the annular plenum. The method may comprise controlling delivery of the ventilation gas output by the jet nozzle in response to a patient airway pressure $P_{sense}$ sensed by the pressure sensor.

Another aspect of the embodiments of the present disclosure is a method of correcting a sensed patient airway pressure $P_{sense}$ in a patient ventilation interface. The method may comprise providing a patient ventilation interface including a nasal pillow body, the nasal pillow body defining a venturi throat that is open to ambient air and having a nasal pillow portion disposed around the throat to define a plenum within the nasal pillow body and outside the venturi throat, the patient ventilation interface further including a jet nozzle arranged to output ventilation gas into the venturi throat. The method may comprise sensing a patient airway pressure $P_{sense}$ in a pressure sensing tube having a pressure sensing port positioned to be in fluid communication with the plenum and correcting for an expected error in the sensed patient airway pressure $P_{sense}$ by applying a correction factor $P_{delta}$ indexed by the sensed patient airway pressure $P_{sense}$. The correction factor $P_{delta}$ may be further indexed by a jet nozzle flow $V'_n$ of the jet nozzle.

Another aspect of the embodiments of the present disclosure is a method of non-invasive ventilation. The method may comprise providing a patient ventilation interface including a nasal pillow body, the nasal pillow body defining a venturi throat that is open to ambient air and having a nasal pillow portion disposed around the throat to define a plenum within the nasal pillow body and outside the venturi throat, the patient ventilation interface further including a jet nozzle arranged to output ventilation gas into the venturi throat. The method may comprise sensing a patient airway pressure $P_{sense}$ in a pressure sensing tube having a pressure sensing port positioned to be in fluid communication with the plenum and controlling delivery of the ventilation gas output by the jet nozzle in response to a patient airway pressure $P_{sense}$ sensed by the pressure sensor.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 12 is a top view of the patient ventilation interface of FIG. 9 showing a stretch capability of the spacer;

FIG. 12A depicts an exemplary stretch setting of the patient ventilation interface shown in FIG. 9;

FIG. 13 is a perspective view of the patient ventilation interface of FIG. 9 showing a twist capability of the spacer;

FIG. 13A depicts an exemplary twist setting of the patient ventilation interface shown in FIG. 9;

DETAILED DESCRIPTION

The present disclosure encompasses various embodiments of a patient ventilation interface of the nasal pillows type for use in a non-invasive ventilation system, along with systems and methods for accurate pressure measurement using the patient ventilation interface. The detailed description set forth below in connection with the appended drawings is intended as a description of several currently contemplated embodiments and is not intended to represent the only form in which the disclosed interface may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
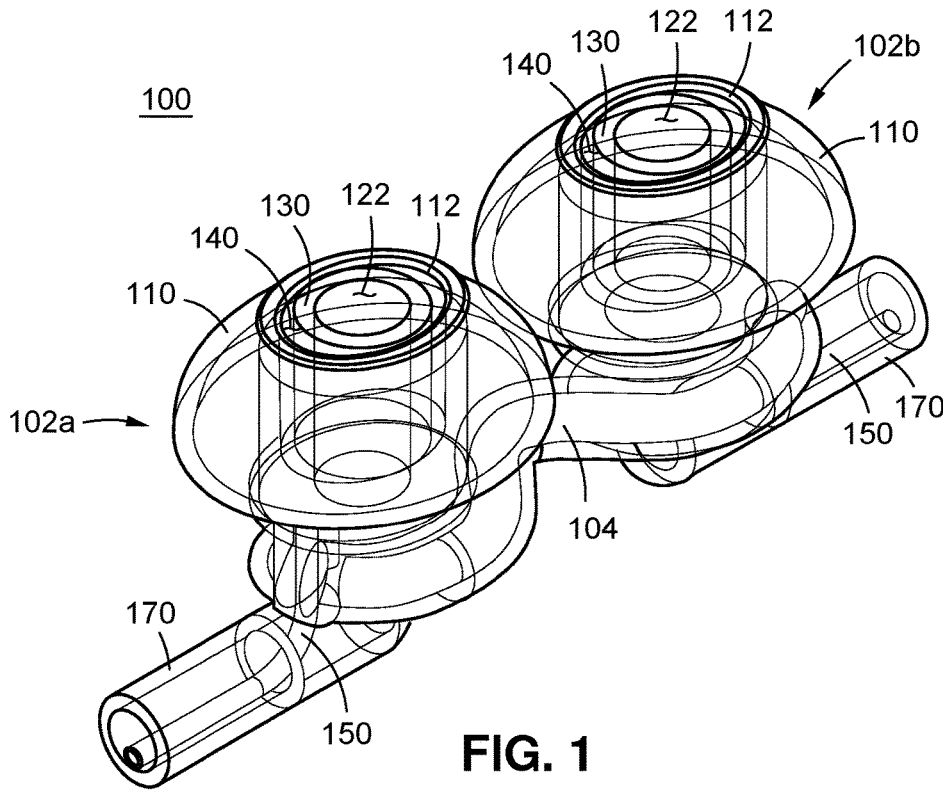
FIG. 1 is a perspective view of an exemplary patient ventilation interface according to an embodiment of the present disclosure.
Figure 2:
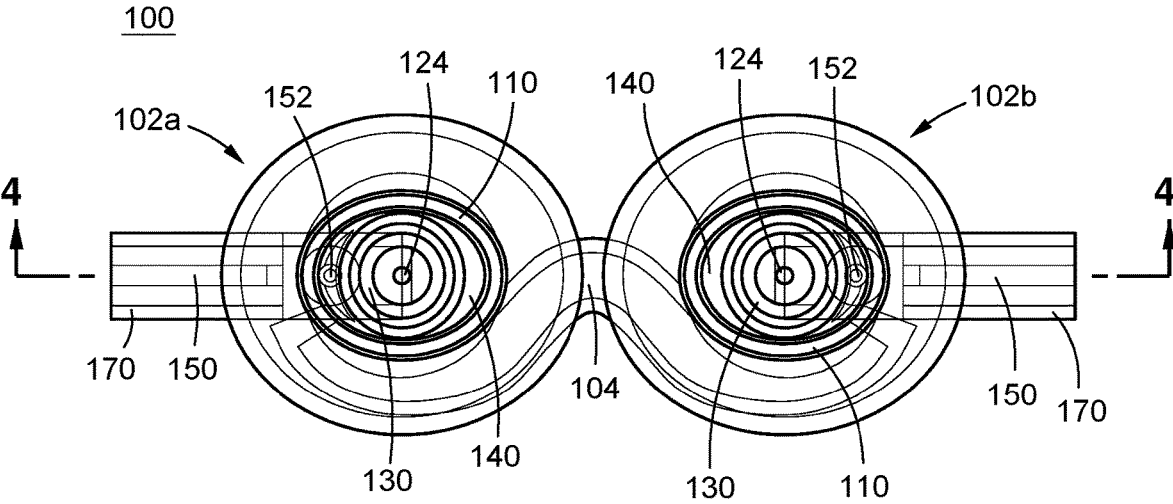
FIG. 2 is a top view of the patient ventilation interface shown in FIG. 1.
Figure 3:
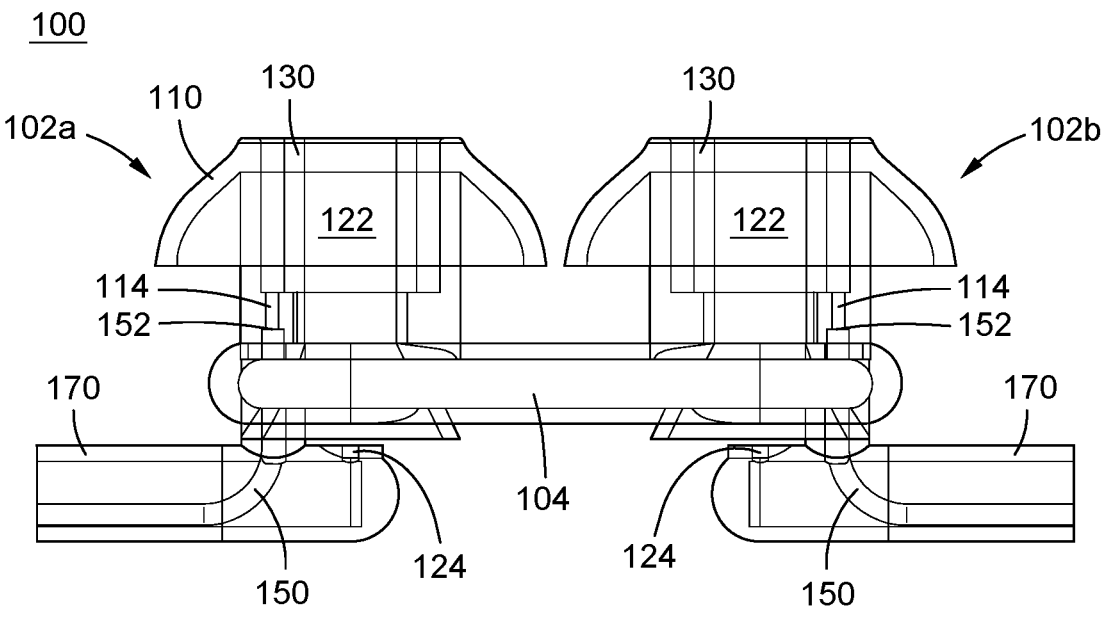
FIG. 3 is a front view of the patient ventilation interface shown in FIG. 1.

FIG. 1 is a perspective view of an exemplary patient ventilation interface 100 according to an embodiment of the present disclosure. FIGS. 2 and 3 are top and side views of the patient ventilation interface 100, respectively. As illustrated, the patient ventilation interface 100 may be of a nasal pillows type defined by a pair of nasal pillows 110 that are configured to be inserted at least partially into the patient's nares or nostrils. The pair of nasal pillows 110 may be provided respectively for left and right pillow assemblies 102a, 102b of the patient ventilation interface 100, which may be symmetrically configured and spaced apart by a spacer 104 to fit into the patient's left and right nostrils. Each nasal pillow 110 may be made of a flexible material such as an elastomer that conforms to the inside of the patient's nostril and creates a seal to prevent leakage between the nasal pillow 110 and the nostril during use. To this end, each nasal pillow 110 may be bell-shaped or otherwise taper outwardly so as to fit more snugly the further it is inserted into the nostril. Delivery of ventilation gas to the patient may be achieved via a pair of jet venturis 120 incorporated into respective ones of the left and right pillow assemblies 102a, 102b of the patient ventilation interface 100, each comprising a venturi throat 122 that is open to ambient air and one or more jet nozzles 124 arranged to output ventilation gas into the venturi throat 122. In this regard, as most clearly illustrated in the cross-sectional views of FIGS. 4 and 5, the nasal pillow 110 of each pillow assembly 102a, 102b may be disposed around a throat body 130 that defines the venturi throat 122 of a corresponding jet venturi 120. Ventilation gas exiting the venturi throat 122 may pass through an opening 112 defined in the corresponding nasal pillow 110 to enter the patient's nostril (with the throat body 130 itself protruding through the opening 112 in some cases).

Figure 4:
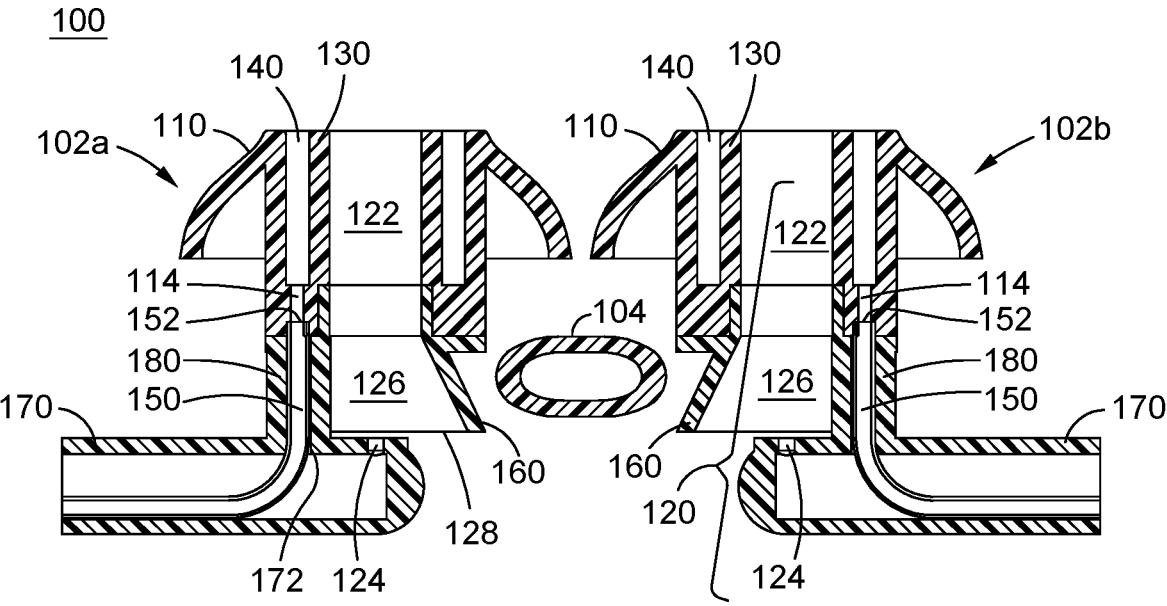
FIG. 4 is a cross-sectional front view of the patient ventilation interface shown in FIG. 3.
Figure 5:
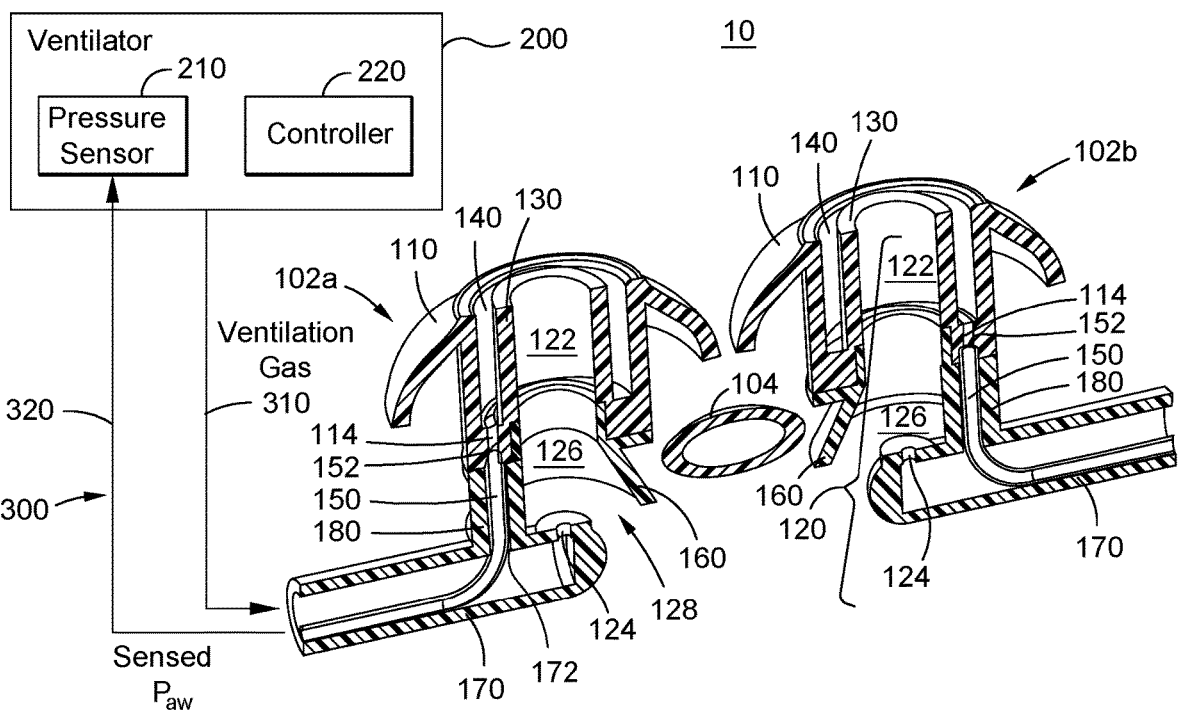
FIG. 5 is a cross-sectional perspective view of the patient ventilation interface of FIGS. 1-4 shown in relation to other elements of a non-invasive ventilation system according to an embodiment of the present disclosure.

In order to provide for accurate pressure sensing within the patient ventilation interface 100, each nasal pillow 110 may be disposed around the corresponding throat body 130 so as to define an annular plenum 140 between the throat body 130 and the nasal pillow 110. It has been found that the pressure within the annular plenum 140 approximates the patient's actual airway pressure $P_{aw}$ with a consistent, predictable error. In order to sense the pressure within the annular plenum 140, the patient ventilation interface 100 may include, in each pillow assembly 102a, 102b (or in some cases only in one of them), a pressure sensing tube 150 having a distal pressure sensing port 152 positioned to be in fluid communication with the annular plenum 140. The pressure sensing port 152 of the pressure sensing tube 150 may be positioned within the annular plenum 140 or may communicate with the annular plenum 140 indirectly, such as via a pressure sensing passage 114 defined by the corresponding nasal pillow 110 as shown in FIGS. 4 and 5.

Preferably, the pressure sensing port 152 is positioned outside the annular plenum 140 using the pressure sensing passage 114 as the communication medium, or just within the annular plenum 140 at or near the base thereof (and hence the base of the nasal pillow 110), as it has been found that there is greater turbulence the farther into the annular plenum 140 the measurement is taken (i.e. the nearer to the patient), making accurate measurement increasingly difficult. By providing the annular plenum 140 and sensing the patient airway pressure therein using the pressure sensing port 152 of the pressure sensing tube 150 as oriented in the above-described manner, the patient ventilation interface 100 avoids the difficulty of accurately sensing pressure within the jet venturi 120 itself, where gas velocity and fluid dynamics are greatest. At the same time, it is not necessary for a sense line to protrude past the nasal pillow 110 and into the patient's nostril, which could be uncomfortable and off-putting to the patient and would not necessarily guarantee that the sensing location is a low velocity region in any case.

Each pillow assembly 102a, 102b may further include an entry piece 160 defining a venturi inlet 126 that is in fluid communication with the venturi throat 122 of the corresponding jet venturi 120. The jet nozzle(s) 124 may be arranged to output the ventilation gas into the venturi throat 122 via the venturi inlet 126. As best understood from FIG. 5, the entry piece 160 may include a generally frustoconical portion that defines an outward flaring of the venturi inlet 126 relative to the venturi throat 122, with the venturi throat 122 being open to ambient air by one or more entrainment openings 128 in the entry piece 160. Because the venturi inlet 126 flares outward relative to the venturi throat 122, the venturi throat 122 presents a constriction to the flow of ventilation gas. Due to the increased velocity of the ventilation gas at the constriction, there is a decrease in pressure that causes ambient air to be entrained via the one or more entrainment openings 128. By amplifying the ventilation gas output by the jet nozzle(s) 124 in this way, the jet venturi 120 may serve as an efficient flow generator when providing ventilation therapy to the patient. At the same time, the one or more entrainment openings 128 may additionally serve as exhalation ports for the patient to exhale through while undergoing ventilation therapy.

In the illustrated example, the jet venturi 120 of each pillow assembly 102a, 102b defines a single entrainment opening 128 which has a generally annular profile and spans almost a full 360°. The corresponding jet nozzle 124 is arranged to output the ventilation gas into the venturi inlet 126 via this entrainment opening 128, such that the ambient air drawn into the entrainment opening 128 flows about the periphery of the jet nozzle 110. With such an arrangement, the jet nozzle 124 may be positioned outside the entrainment opening 128 as shown or may protrude into the venturi inlet 126 though the entrainment opening 128 so as to reside downstream of the entrainment opening 128. In addition to or instead of this arrangement, it is also contemplated that one or more entrainment openings 128 may be formed in a side wall of the entry piece 160 such that the ambient air drawn into the entrainment opening(s) 128 flows in a side-by-side or parallel relationship with the ventilation gas delivered by the jet nozzle 124.

The ventilation gas may be provided to the patient ventilation interface 100 via a pair of ventilation gas tubes 170, each of which terminates in a respective jet nozzle 124 (or a respective plurality of jet nozzles 124 in a case where each jet venturi 120 has more than one jet nozzle 124). The ventilation gas may be provided by a ventilation gas source such as a ventilator 200 (see FIG. 5). Exemplary ventilators and associated oxygen concentrators that may be used with the disclosed embodiments include those described in U.S. Pat. No. 9,132,250, entitled METHODS, SYSTEMS AND DEVICES FOR NON-INVASIVE VENTILATION INCLUDING A NON-SEALING VENTILATION INTERFACE WITH AN ENTRAINMENT PORT AND/OR PRESSURE FEATURE; U.S. Pat. No. 9,675,774, entitled METHODS, SYSTEMS AND DEVICES FOR NON-INVASIVE OPEN VENTILATION WITH GAS DELIVERY NOZZLES IN FREE SPACE; U.S. Pat. No. 9,962,512, entitled METHODS, SYSTEMS AND DEVICES FOR NON-INVASIVE VENTILATION INCLUDING A NON-SEALING VENTILATION INTERFACE WITH A FREE SPACE NOZZLE FEATURE; U.S. Pat. No. 10,369,320, entitled MODULAR VENTILATION SYSTEM; U.S. Patent Application Pub. No. 2019/0307981, entitled MODULAR VENTILATION SYSTEM; and U.S. patent application Ser. No. 16/874,472, filed May 14, 2020 and entitled O2 CONCENTRATOR WITH SIEVE BED BYPASS AND CONTROL METHOD THEREOF, the entire contents of each of which are expressly incorporated herein by reference.

In order to minimize the number of exposed tubes, at least a part of each pressure sensing tube 150 may be disposed within a respective one of the ventilation gas tubes 170. Each pressure sensing tube 150 may then branch off from the corresponding ventilation gas tube 170 to be directed toward the annular plenum 140 and/or pressure sensing passage 114 of the associated nasal pillow 110. To this end, each ventilation gas tube 170 may have an opening 172 in a side wall thereof at a location prior to where the ventilation gas tube 170 terminates in the corresponding jet nozzle 124, and the associated pressure sensing tube 150 may pass through the opening 172 to extend from the ventilation gas tube 170 into or toward the nasal pillow 110. In order to route the pressure sensing tube 150 from the ventilation gas tube 170 to the annular plenum 140 or pressure sensing passage 114, each pillow assembly 102a, 102b may further include a sheath 180. As shown in FIG. 5, the sheath 180 of each pillow assembly 102a, 102b may connect the opening 172 in the side wall of the corresponding ventilation gas tube 170 with the associated nasal pillow 110 and, as such, may interrupt the frustoconical portion of the entry piece 160 at a position along a perimeter thereof. This is the reason the entrainment opening 128 may span almost, but not a full, 360° as indicated above. The sheath 180 may also serve to attach the ventilation gas tube 170 to the remainder of the corresponding pillow assembly 102a, 102b.

As shown schematically in FIG. 5, the delivery of ventilation gas to the jet nozzles 124 of the pillow assemblies 102a, 102b may be facilitated via several segments of multi-lumen tubing 300, each segment of multi-lumen tubing 300 defining at least a ventilation gas lumen 310 and a pressure sensing lumen 320. In an exemplary system architecture, two separate segments of the multi-lumen tubing 300 are fluidly connected to the patient ventilation interface 100 such that the ventilation gas lumens 310 defined thereby fluidly communicate with respective ones of the ventilation gas tubes 170, while the pressure sensing lumens 320 fluidly communicate with respective ones of the pressure sensing tubes 150 residing within corresponding ones of the ventilation gas tubes 170. As an alternative to the exemplary ventilation gas tube 170, which houses the pressure sensing tube 150 as shown in the drawings, it is contemplated that the ventilation gas tube 170 may itself be a multi-lumen tube that is connectable to or integrated with the corresponding segment of the multi-lumen tubing 300 and that includes separate lumens for delivering the ventilation gas and sensing pressure, the latter of which terminates at the opening 172. In such a case, the pressure sensing tube 150 may simply extend from the opening 172 of the ventilation gas tube 170 to the corresponding annular plenum 140 or pressure sensing passage 114 of the nasal pillow 110, without being disposed in the ventilation gas tube 170 at all.

In order to determine the patient's airway pressure, a system 10 including the patient ventilation interface 100 may further include a pressure sensor 210 fluidly coupled to the pressure sensing tubes 150 of the patient ventilation interface 100. In the exemplary non-invasive ventilation system 10 shown in FIG. 5, for example, the pressure sensor 210 is located within the ventilator 200 as described above. The pressure sensor 210 may sense the pressure $P_{sense}$ in the annular plenums 140 at the positions of the pressure sensing ports 152 of the pressure sensing tubes 150, or indirectly via the pressure sensing passages 114 formed in the nasal pillows 110. The pressure $P_{sense}$ may be referred to as the sensed patient airway pressure $P_{sense}$ and may approximate the actual patient airway pressure $P_{aw}$ in the airway of the patient. The sensed patient airway pressure $P_{sense}$ may be detectable by the pressure sensor 210 over the pressure sensing tubes 150 and pressure sensing lumens 320 of the above-described segments of the multi-lumen tubing 300 according to the movement of a diaphragm within the pressure sensor 210, for example. Along these lines, in the exemplary system architecture shown schematically in FIG. 5, it is contemplated that the two separate segments of multi-lumen tubing 300 which are fluidly connected to the patient ventilation interface 100 as described above will each also be fluidly connected to respective branches of a Y-connector, the remaining branch of which is fluidly connected to the ventilator 200 via a third separate segment of the multi-lumen tubing 300. The pressure sensing lumen 320 defined by this third segment of the multi-lumen tubing 300 is fluidly coupled to the pressure sensor 210 of the ventilator 200. As will be recognized, the integration of the Y-connector into the exemplary system architecture effectively bifurcates the pressure sensing lumen 320 extending directly to the pressure sensor 210 into the pair of pressure sensing lumens 320 defined by respective ones of each of the two remaining segments of the multi-lumen tubing 300 extending directly to the patient ventilation interface 100. In a similar manner, the Y-connector effectively bifurcates the ventilation gas lumen 310 extending directly to the ventilator 200 into the pair of ventilation gas lumens 310 defined by respective ones of each of the two remaining segments of the multi-lumen tubing 300 extending directly to the patient ventilation interface 100, thus providing a ventilation gas flow path from the ventilator 200 to the jet nozzle(s) 124 of each jet venturi 120.

As further shown in FIG. 5, the system 10 may additionally include a controller 220 programmed to control delivery of the ventilation gas output by the jet nozzle(s) 124 in response to the patient airway pressure $P_{sense}$ sensed by the pressure sensor 210. The sensed patient airway pressure $P_{sense}$ may be used for pressure triggering, for example, in which the controller 220 may deliver a breath of ventilation gas at a specific phase of the patient's breathing, typically during inhalation, or to provide positive end-expiratory pressure (PEEP) during an exhalation phase. The controlled delivery of the ventilation gas may be on a pre-set time-based schedule. As noted above, the sensed patient airway pressure $P_{sense}$ within the annular plenums 140 approximates the patient's actual airway pressure $P_{aw}$ with a consistent, predictable error. The controller 220 may be programmed to correct for the expected error, for example, by applying a correction factor $P_{delta}$ indexed by the sensed patient airway pressure $P_{sense}$, where the actual patient airway pressure $P_{aw}$ can be approximated as $P_{aw}=P_{sense}+P_{delta}$.

Figure 6:
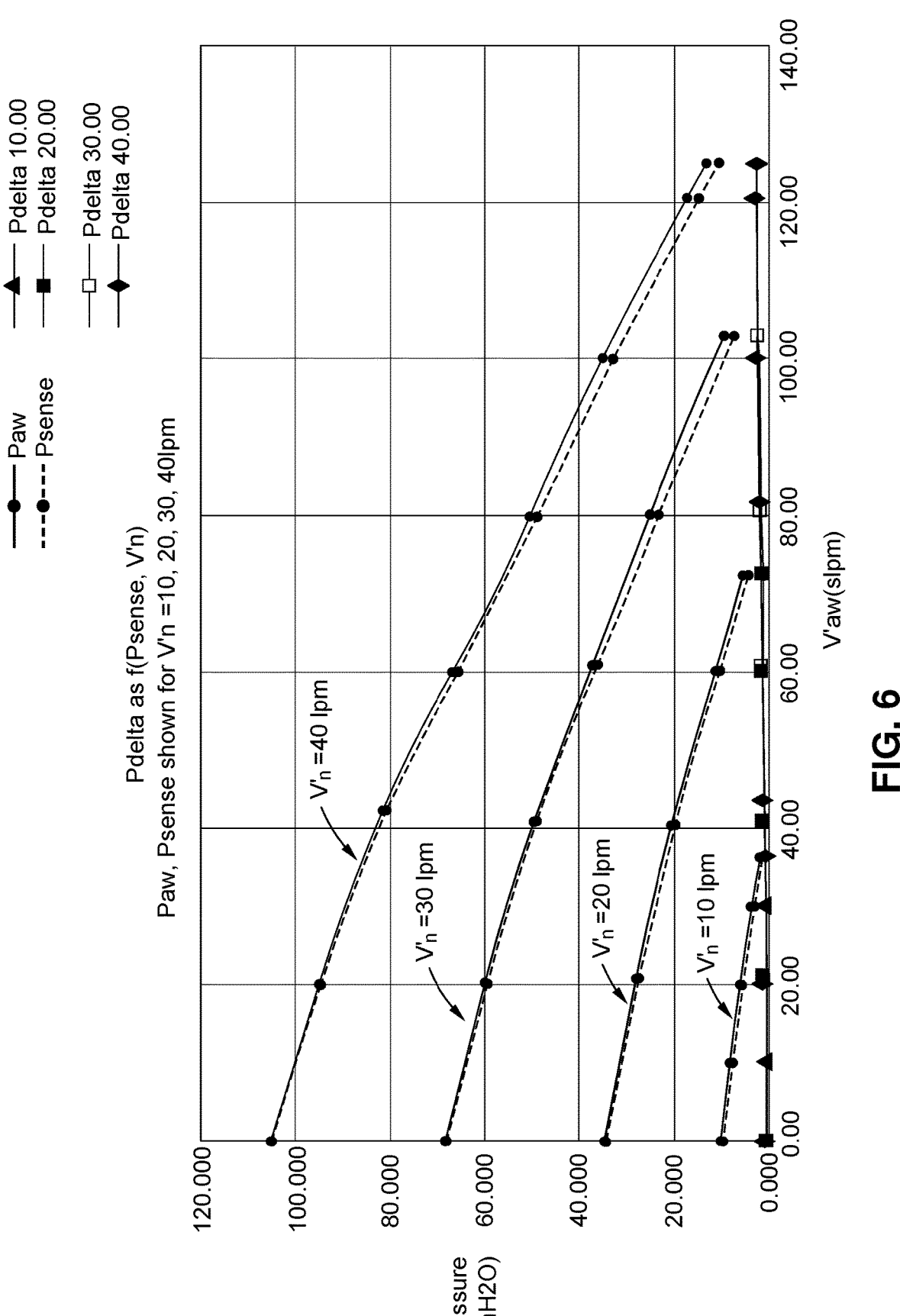
FIG. 6 graphically depicts exemplary performance characteristics of the patient ventilation interface.

FIG. 6 graphically depicts exemplary performance characteristics of the patient ventilation interface 100 at a variety of settings of jet nozzle flow $V'_n$ representing a total airflow of ventilation gas output by the jet nozzle(s) 124. For each jet nozzle flow $V'_n$ (10.00 slpm, 20.00 slpm, 30.00 slpm, and 40.00 slpm), the sensed patient airway pressure $P_{sense}$ is shown in comparison to the actual patient airway pressure $P_{aw}$ at various values of patient airway flow $V'_{aw}$ (which can be simulated using a variable resistance, for example). On the same graph, the difference between the actual patient airway pressure $P_{aw}$ and the sensed patient airway pressure $P_{sense}$ is plotted as $P_{delta}$, representing the correction factor for correcting the sensed patient airway pressure $P_{sense}$. The same data is provided below in Table 1.

TABLE 1

| $V'_n$ (slpm) | $P_v$ (psi) | $V'_{aw}$ (slpm) | $P_{aw}$ (cmH2O) | $P_{sense}$ (cmH2O) | $P_{delta}$ (cmH2O) |
|---|---|---|---|---|---|
| 10.00 | 1.7 | 36.32 | 1.916 | 1.300 | 0.616 |
| 10.00 | 1.7 | 30.00 | 3.549 | 3.000 | 0.549 |
| 10.00 | 1.7 | 20.05 | 6.123 | 5.600 | 0.523 |
| 10.00 | 1.7 | 10.03 | 8.265 | 7.900 | 0.365 |
| 10.00 | 1.7 | 0.00 | 10.032 | 9.700 | 0.332 |
| 20.00 | 6.3 | 72.30 | 5.450 | 4.300 | 1.150 |
| 20.00 | 6.3 | 60.12 | 11.199 | 10.300 | 0.899 |
| 20.00 | 6.3 | 40.31 | 20.309 | 19.700 | 0.609 |
| 20.00 | 6.3 | 20.71 | 27.927 | 27.500 | 0.427 |
| 20.00 | 6.3 | 0.00 | 34.751 | 34.500 | 0.251 |
| 30.00 | 12.6 | 102.94 | 9.502 | 7.200 | 2.302 |
| 30.00 | 12.6 | 80.04 | 24.965 | 23.300 | 1.665 |
| 30.00 | 12.6 | 60.88 | 37.303 | 36.200 | 1.103 |
| 30.00 | 12.6 | 40.87 | 49.650 | 49.000 | 0.650 |
| 30.00 | 12.6 | 20.25 | 59.775 | 59.500 | 0.275 |
| 30.00 | 12.6 | 0.00 | 68.200 | 68.100 | 0.100 |
| 40.00 | 19.9 | 125.00 | 13.140 | 10.500 | 2.640 |
| 40.00 | 19.9 | 120.59 | 17.232 | 14.700 | 2.532 |
| 40.00 | 19.9 | 100.02 | 35.015 | 33.000 | 2.015 |
| 40.00 | 19.9 | 79.78 | 50.555 | 48.900 | 1.655 |
| 40.00 | 19.9 | 59.99 | 66.850 | 65.700 | 1.150 |
| 40.00 | 19.9 | 42.32 | 81.566 | 80.800 | 0.766 |
| 40.00 | 19.9 | 20.04 | 94.950 | 94.700 | 0.250 |
| 40.00 | 19.9 | 0.00 | 105.115 | 104.900 | 0.215 |

Regression analysis on all $V'_{aw}$-$P_{aw}$, $V'_{aw}$-$P_{sense}$, and $V'_{aw}$-$P_{delta}$ curves of FIG. 6 yields linear trendlines with high coefficients of determination (e.g. R-square>0.99). In principle, the $V'_{aw}$-$P_{delta}$ curves may be generalized by Equations 1-4, below, where $m_{40}$, $m_{30}$, $m_{20}$, and $m_{10}$ are the slopes of the linear trendlines and $b_{40}$, $b_{30}$, $b_{20}$, and $b_{10}$ are the y-intercepts of the linear trendlines at each respective jet nozzle flow $V'_s$, as determined from the regression analysis:

$$P_{delta}=m_{40}V'_{aw}+b_{40}, \text{ when } V'_n=40 \text{ slpm} \quad \text{(Eq. 1)}$$

$$P_{delta}=m_{30}V'_{aw}+b_{30}, \text{ when } V'_n=30 \text{ slpm} \quad \text{(Eq. 2)}$$

$$P_{delta}=m_{20}V'_{aw}+b_{20}, \text{ when } V'_n=20 \text{ slpm} \quad \text{(Eq. 3)}$$

$$P_{delta}=m_{10}V'_{aw}+b_{10}, \text{ when } V'_n=10 \text{ slpm} \quad \text{(Eq. 4)}$$

Compensating $P_{sense}$ using the above equations, that is, approximating $P_{aw}$ as $P_{aw}=P_{sense}+P_{delta}$ for arbitrary $V'_{aw}$, yields an approximate $P_{aw}$ that is within measurement accuracy requirements of $\pm(2 \text{ cmH}_2\text{O}+4\%)$.

In practice, however, $V'_n$ may vary arbitrarily within some range and $V'_{aw}$ may be unknown. Therefore, in the context of the non-invasive ventilation system 10, the controller 220 may determine the correction factor $P_{delta}$ for arbitrary $V'_n$ and with unknown $V'_{aw}$. To demonstrate this, the remaining linear trendlines may be generalized as shown in Table 2, below:

TABLE 2

| $V'_n$ | $V'_{aw}$-$P_{aw}$ | $V'_{aw}$-$P_{sense}$ | $V'_{aw}$-$P_{delta}$ (Eqs. 1-4) |
|---|---|---|---|
| 40 slpm | $P_{aw} = m_{a40}V'_{aw} + b_{a40}$ | $P_{sense} = m_{s40}V'_{aw} + b_{s40}$ | $P_{delta} = m_{40}V'_{aw} + b_{40}$ |
| 30 slpm | $P_{aw} = m_{a30}V'_{aw} + b_{a30}$ | $P_{sense} = m_{s30}V'_{aw} + b_{s30}$ | $P_{delta} = m_{30}V'_{aw} + b_{30}$ |
| 20 slpm | $P_{aw} = m_{a20}V'_{aw} + b_{a20}$ | $P_{sense} = m_{s20}V'_{aw} + b_{s20}$ | $P_{delta} = m_{20}V'_{aw} + b_{20}$ |
| 10 slpm | $P_{aw} = m_{a10}V'_{aw} + b_{a10}$ | $P_{sense} = m_{s10}V'_{aw} + b_{s10}$ | $P_{delta} = m_{10}V'_{aw} + b_{10}$ |

As the common variable is $V'_{aw}$, $P_{delta}$ may be represented as a function of $P_{sense}$ using the $V'_{aw}$-$P_{sense}$ and $V'_{aw}$-$P_{delta}$ trendlines. That is, in the case of $V'_n$=40 slpm, $$P_{sense}=m_{s40}V'_{aw}+b_{s40}$$

can be rearranged to find $$V'_{aw} = \left(\frac{1}{m_{s40}}\right)P_{sense} - \left(\frac{b_{s40}}{m_{s40}}\right)$$

which can be plugged into Equation 1 to find $$P_{delta} = m_{40}\left(\left(\frac{1}{m_{s40}}\right)P_{sense} - \left(\frac{b_{s40}}{m_{s40}}\right)\right) + b_{40}$$

which reduces to the following linear equation:

$$P_{delta} = \left(\frac{m_{40}}{m_{s40}}\right)P_{sense} + b_{40} - \frac{m_{40}b_{s40}}{m_{s40}}$$

Rewriting $P_{delta}$ as a function of $P_{sense}$ for each of the values of $V'_n$ in the same fashion yields four linear functions, tabulated in Table 3, below:

TABLE 3

| $V'_n$ | Coefficient A (slope) | Coefficient B (y-intercept) |
|---|---|---|
| 40 slpm | $A_{40} = \frac{m_{40}}{m_{s40}}$ | $B_{40} = b_{40} - \frac{m_{40}b_{s40}}{m_{s40}}$ |
| 30 slpm | $A_{30} = \frac{m_{30}}{m_{s30}}$ | $B_{30} = b_{30} - \frac{m_{30}b_{s30}}{m_{s30}}$ |
| 20 slpm | $A_{20} = \frac{m_{20}}{m_{s20}}$ | $B_{20} = b_{20} - \frac{m_{20}b_{s20}}{m_{s20}}$ |
| 10 slpm | $A_{10} = \frac{m_{10}}{m_{s10}}$ | $B_{10} = b_{10} - \frac{m_{10}b_{s10}}{m_{s10}}$ |

Figure 7:
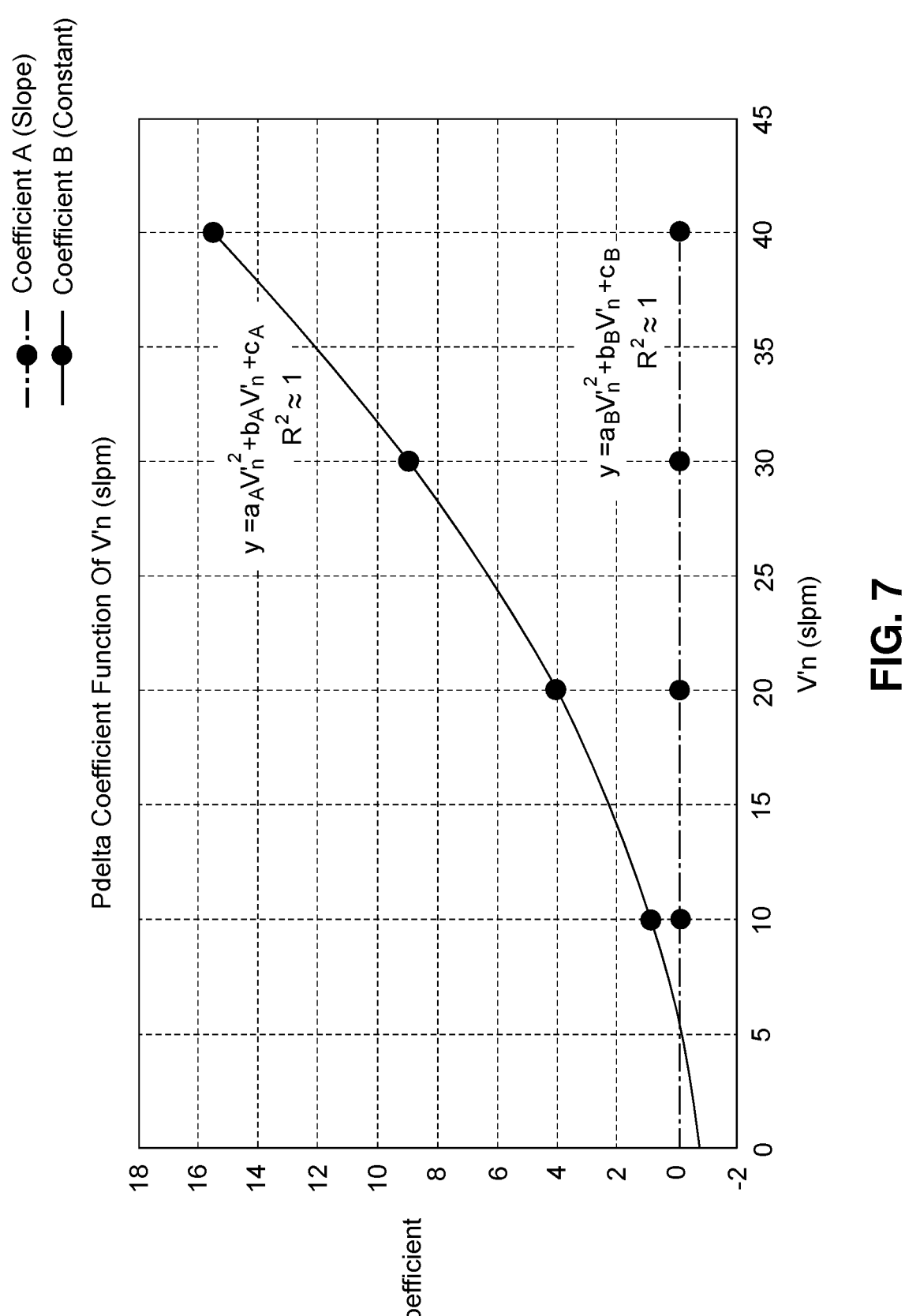
FIG. 7 shows trendlines of coefficients for determining a correction factor for a patient airway pressure sensed using the patient ventilation interface.

As illustrated in FIG. 7, the coefficients $A_{40}$, $A_{30}$, $A_{20}$, and $A_{10}$ and the coefficients $B_{40}$, $B_{30}$, $B_{20}$, and $B_{10}$ can then be charted to determine trendlines for Coefficient A and Coefficient B as a function of the jet nozzle flow $V'_n$ by regression analysis:

$$\text{Coefficient } A = a_A V_n'^2 + b_A V_n' + c_A \qquad \text{(Eq. 5)}$$

$$\text{Coefficient } B = a_B V_n'^2 + b_B V_n' + c_B \qquad \text{(Eq. 6)}$$

These two polynomial equations, whose coefficients $a_A$, $a_B$, $b_A$, $b_B$, $c_A$, and $c_B$ are known from regression analysis of the data in FIG. 7, can be used to generate coefficients A and B for any arbitrary $V'_n$, which can then be used to evaluate a general equation for $P_{delta}$ as a function of $P_{sense}$:

$$P_{delta}=AP_{sense}+B \qquad \text{(Eq. 7)}$$

Using Equation 7, the correction factor $P_{delta}$ for any sensed patient airway pressure $P_{sense}$ may be calculated. Finally, the actual patient airway pressure $P_{aw}$ may be approximated by adding the measured patient airway pressure $P_{sense}$ to the calculated correction factor $P_{delta}$ according to $P_{aw}=P_{sense}+P_{delta}$. Because the patient airway pressure $P_{sense}$ is sensed in the annular plenums 140 as described above, where the fluid dynamics are reduced relative to the space within each jet venturi 120 itself, the resulting approximated patient airway pressure $P_{aw}$ will be within measurement accuracy requirements of $\pm(2 \text{ cmH}_2\text{O}+4\%)$.

As demonstrated by the above exemplary procedure for determining the correction factor $P_{delta}$, the controller 220 of the system 10 may be programmed to correct for the expected error in the sensed pressure $P_{sense}$ by applying a correction factor $P_{delta}$, which may in general be a second order polynomial of the form $P_{delta}$=f($V'_n$, $P_{sense}$). The correction factor $P_{delta}$ may be indexed by the sensed patient airway pressure $P_{sense}$ (e.g. per Eq. 7) and may be further indexed by the jet nozzle flow $V'_n$ of the jet nozzle(s) 124 (e.g. per Eqs. 5 and 6). It is noted that the controller 220 may perform calculations and/or reference pre-calculated lookup tables to determine the correction factor $P_{delta}$ given an input of $P_{sense}$ and/or $V'_n$, with any such combination of methodologies falling within the meaning of the correction factor $P_{delta}$ being indexed by $P_{sense}$ and/or $V'_n$.

Figure 8:
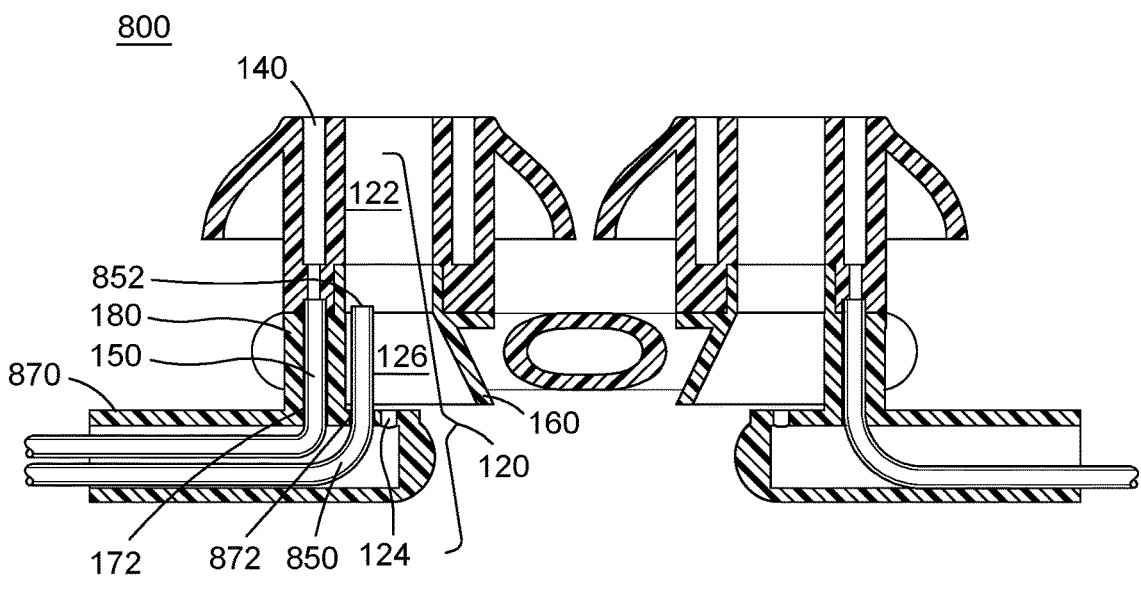
FIG. 8 is a cross-sectional front view of another exemplary patient ventilation interface according to an embodiment of the present disclosure.

FIG. 8 is a cross-sectional front view of another exemplary patient ventilation interface 800 according to an embodiment of the present disclosure. The patient ventilation interface 800 may likewise be integrated into a system 10 such as the exemplary non-invasive ventilation system 10 including the ventilator 200 and multi-lumen tubing 300 shown in FIG. 5. However, in contrast to the patient ventilation interface 100, the patient ventilation interface 800 may further incorporate a second pressure sensing tube 850 in one of the left and right pillow assemblies 102a, 102b, in addition to the first pressure sensing tube 150, for sensing the inlet pressure of the corresponding jet venturi 120. For example, a pressure sensing port 852 of the second pressure sensing tube 850 may be positioned to be in fluid communication with a negative pressure region of the jet venturi 120 such as within the venturi inlet 126 or just within the venturi throat 122 and outside a cone of ventilation gas output by the associated jet nozzle(s) 124.

In place of one of the ventilation gas tubes 170 of the patient ventilation interface 100, the patient ventilation interface 800 of FIG. 8 may have a ventilation gas tube 870. The ventilation gas tube 870 may be the same as the ventilation gas tube 170 except for the further inclusion of a second opening 872 in a side wall thereof. Like the first pressure sensing tube 150, at least a part of the second pressure sensing tube 850 may be disposed within the ventilation gas tube 870. The second pressure sensing tube 850 may then branch off from the ventilation gas tube 870 to be directed toward the venturi throat 122 through the corresponding entry piece 160. To this end, the second opening 872 in the side wall of the ventilation gas tube 870 may be at a location after the first opening 172 but prior to where the ventilation gas tube 870 terminates in the jet nozzle(s) 124, and the second pressure sensing tube 850 may pass through the second opening 872. The second pressure sensing tube 850 may be fixed to an outer wall of the corresponding sheath 180 as shown or may be within a similar sheath that extends inside the venturi inlet 126.

By incorporating the second pressure sensing tube 850, a pressure difference can be found between the sensed patient airway pressure $P_{sense}$ in the corresponding annular plenum 140 (or the approximated actual patient airway pressure $P_{aw}=P_{sense}+P_{delta}$) and the throat inlet pressure $P_{in}$ as sensed by the second pressure sensing tube 850. This pressure difference can be used to calculate an airflow through the venturi throat 122 and thus approximate a patient airflow $V'_{aw}$ in the case of both inspiratory flow and exhalation flow. The approximate patient airflow $V'_{aw}$ can then be used to further reduce the error of the approximated patient airway pressure $P_{aw}$ and/or for flow triggering of the ventilator 200, for example.

As will be recognized, the integration of the patient ventilation interface 800 into the system 10 would require that the segment of multi-lumen tubing 300 extending to the ventilation gas tube 870 of the patient ventilation interface 800 (and having its ventilation gas and pressure sensing lumens 310, 320 fluidly connected to respective ones of the ventilation gas and pressure sensing tubes 870, 150) further define a dedicated second pressure sensing lumen in addition to the pressure sensing lumen 320. This second pressure sensing lumen would be placed into fluid communication with the pressure sensing tube 850 and, using the Y-connector, would also be placed into fluid communication with a corresponding second pressure sensing lumen further defined by that segment of the multi-lumen tubing 300 extending between the Y-connector and the ventilator 200. Sensed pressure presented to the ventilator 200 via the second pressure sensing lumens of these two segments of the multi-lumen tubing 300 would be sensed by the pressure sensor(s) 210 independently of that presented via the pressure sensing lumens 320, thus allowing for the calculation of the above-described pressure differential. While it is contemplated that the patient ventilation interface 800 will be outfitted with only one pressure sensing tube 850, those of ordinary skill in the art will recognize that the patient ventilation interface 800 may incorporate a pair of second pressure sensing tubes 850 (and the associated ventilation gas tubes 870) in respective ones of each of the left and right pillow assemblies 102a, 102b. In this instance, the system 10 would require that the two segments of multi-lumen tubing 300 extending to respective ones of the ventilation gas tubes 870 each further define a dedicated second pressure sensing lumen in addition to the pressure sensing lumen 320. These second pressure sensing lumens would be placed into fluid communication with respective ones of the pressure sensing tubes 850 and, using the Y-connector, would also be placed into fluid communication with a corresponding second pressure sensing lumen further defined by that segment of the multi-lumen tubing 300 extending between the Y-connector and the ventilator 200.

Figure 9:
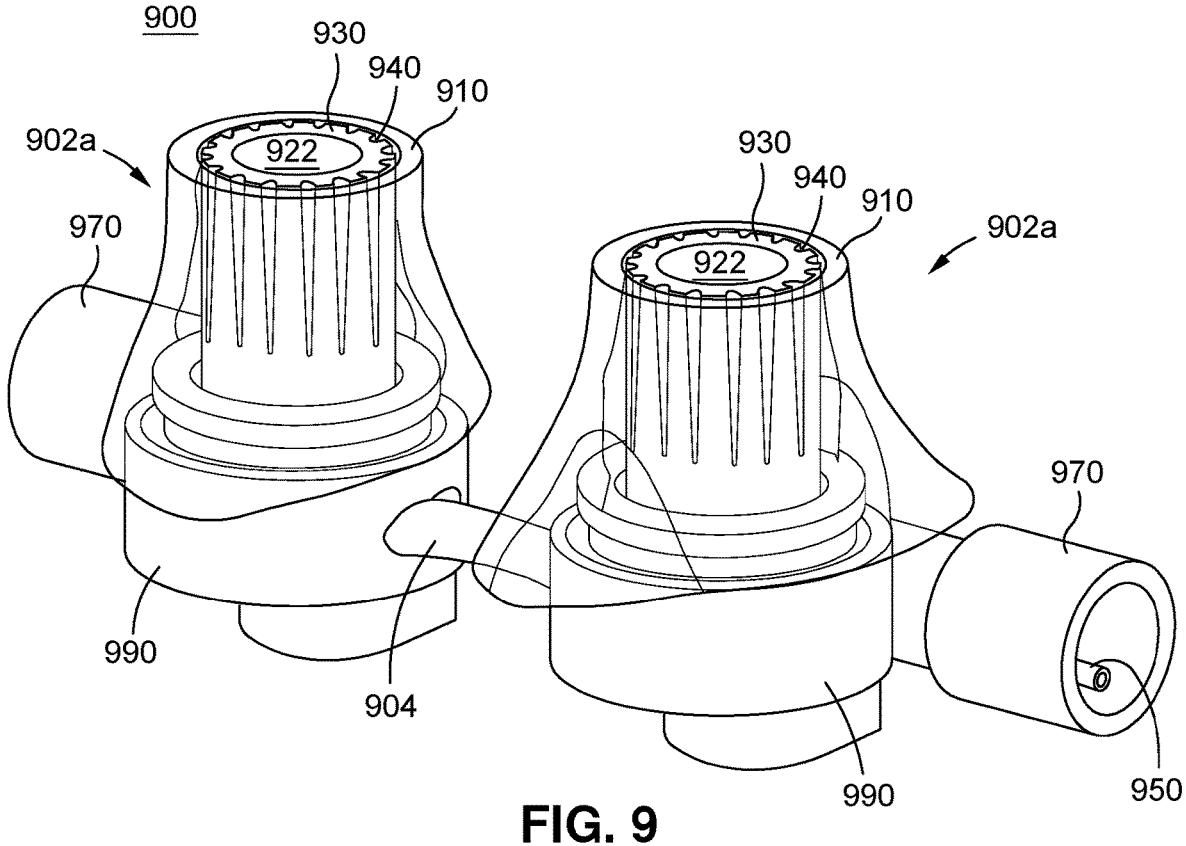
FIG. 9 is a perspective view of another exemplary patient ventilation interface according to an embodiment of the present disclosure.

FIG. 9 is a perspective view of another exemplary patient ventilation interface 900 according to an embodiment of the present disclosure. The patient ventilation interface 900 may likewise be integrated into a system 10 such as the exemplary non-invasive ventilation system 10 including the ventilator 200 and multi-lumen tubing 300 shown in FIG. 5, except that the patient ventilation interface 900 shows an alternative form factor including some additional features, any or all of which may be incorporated into the patient ventilation interfaces 100, 800 described above. For example, while the patient ventilation interface 900 includes a pair of nasal pillows 910 provided respectively for left and right pillow assemblies 902a, 902b, which may be functionally the same as the nasal pillows 110 of the left and right pillow assemblies 102a, 102b shown in FIGS. 1-5 and 8, the nasal pillows 910 are depicted as having an elliptical rather than a circular cross-section. As such, the nasal pillows 910 may better accommodate the anatomical shape of the patient's nostrils for a more comfortable fit and a better seal. To further improve the fit and account for differences in anatomy from patient to patient, it is contemplated that the nasal pillows 910 may be configured to swivel about their respective throat bodies 930 defining the venturi throats 922 (functionally corresponding to the throat bodies 130 of the patient ventilation interfaces 100, 800).

In addition to serving as an axle in the case of a swiveling nasal pillow 910, each throat body 930 further differs from the previously depicted throat body 130 in that the outer surface of the throat body 930 is splined. By providing a splined throat body 930 in this way, it can be assured that the annular plenum 940 defined between the throat body 930 and the nasal pillow 910 (corresponding to the annular plenum 140) does not become closed or collapsed, which could negatively impact the accuracy of the sensed patient airway pressure $P_{sense}$. As such, the splines may render the sensing tube 950 insensitive to occlusions of the nasal pillow 910 with the throat body 930. In greater detail, in accordance with its splined configuration, a series of elongate, vertically extending channels or grooves are formed about the outer surface of the throat body 930 in equidistantly spaced relation to each other, each to a prescribed depth which may be uniform or variable along the length thereof. In a similar manner, the circumferential width of each channel may be uniform, or variable along its length. As seen in FIG. 9, while the channels will preferably extend to the distal end of the throat body 930, it is contemplated that the opposite ends may terminate slightly above the base of the corresponding annular plenum 940. As the throat body 930 may have greater rigidity than the nasal pillow 910 (which is preferably softer for increased patient comfort), the comparatively less rigid nasal pillow 910 may have a greater tendency to resiliently deflect or deform into direct contact with the outer surface the throat body 930 (particularly at the distal region advanced into a nostril), thus potentially fully or partially blocking fluid communication to the corresponding pressure sensing tube(s) 150, 850 at the base of the associated annular plenum 940. As indicated above, the inclusion of the channels effectively prevents any such blockage.

Also depicted in FIG. 9 is an outer housing 990 of each pillow assembly 902a, 902b, which may be used to hide the shape of the functional components (e.g. the entry piece 160) and create a desired form factor for easy manipulation by a patient. In the example shown, the two outer housings 990 are connected by a spacer 904 that may be functionally the same as the spacer 104 described above. Within the outer housings 990, the venturi throats 922 may be fluidly coupled to respective ventilation gas tubes 970 (corresponding to ventilation gas tubes 170), with the annular plenums 940 being fluidly coupled to respective pressure sensing tubes 950 (corresponding to pressure sensing tubes 150).

Figure 10:
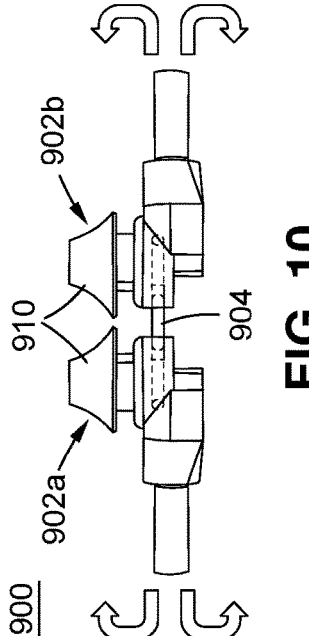
FIG. 10 is a front view of the patient ventilation interface of FIG. 9 showing a vertical bend capability of a spacer integrated therein.
Figure 10A:
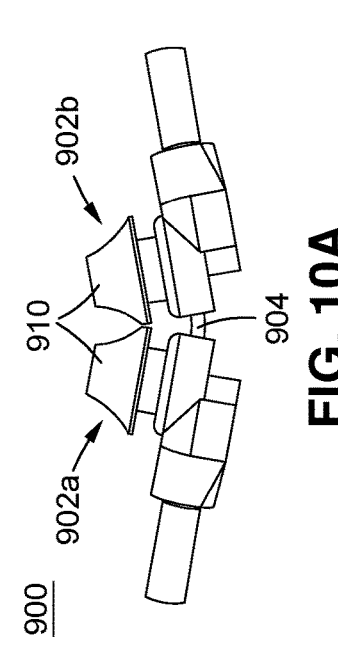
FIG. 10A depicts an exemplary vertical bend setting of the patient ventilation interface shown in FIG. 9.
Figure 10B:
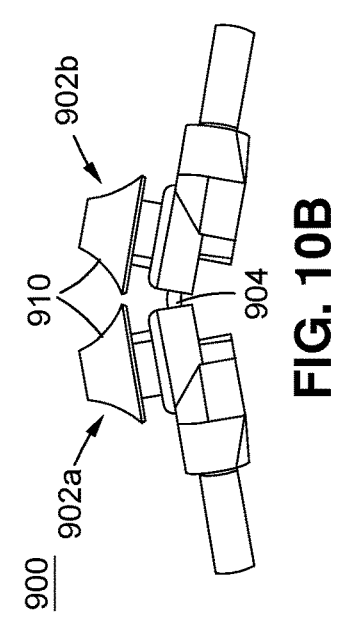
FIG. 10B depicts another exemplary vertical bend setting of the patient ventilation interface shown in FIG. 9.

FIG. 10 is a front view of the patient ventilation interface 900 showing a vertical bend capability of the spacer 904. The spacer 904 may be made of or include a material that is manually deformable and holds its new shape upon being deformed, such as a metal wire (e.g. aluminum) or a shape-memory polymer (e.g. a polymer that only returns to its relaxed state when a specified stimulus is applied such as being heated to a particular temperature or exposed to a particular light). As such, the spacer 904 may have freedom of motion in three dimensions, enabling various adjustments of the patient ventilation interface 900 to accommodate a variety of patient anatomies and preferences, including the vertical bending shown in FIG. 10. FIG. 10A shows an exemplary vertical bend setting of the patient ventilation interface 900 in which the spacer 904 has been bent upward at its ends to bring the nasal pillows 910 inward so that they face each other and sit closer together. FIG. 10B shows another exemplary vertical bend setting of the patient ventilation interface 900 in which the spacer 904 has been bent downward at its ends to move the nasal pillows 910 outward so that they face away from each other and sit farther apart.

Figure 11:
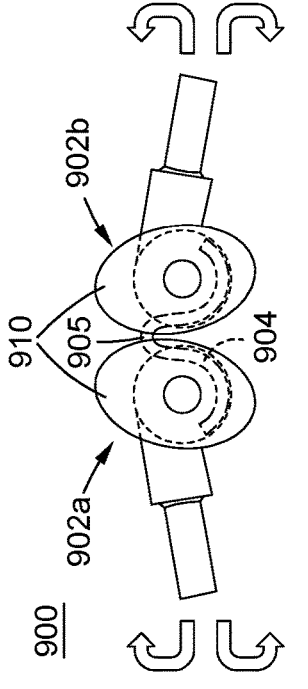
FIG. 11 is a top view of the patient ventilation interface of FIG. 9 showing a horizontal bend capability of the spacer.
Figure 11A:
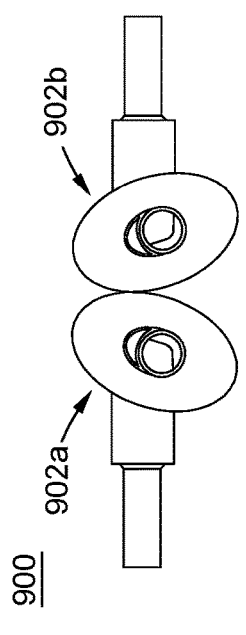
FIG. 11A depicts an exemplary horizontal bend setting of the patient ventilation interface shown in FIG. 9.
Figure 11B:
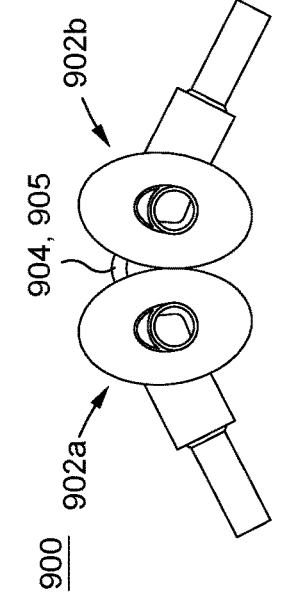
FIG. 11B depicts another exemplary horizontal bend setting of the patient ventilation interface shown in FIG. 9.

FIG. 11 is a top view of the patient ventilation interface 900 showing a horizontal bend capability of the spacer 904. FIG. 11A shows an exemplary horizontal bend setting of the patient ventilation interface 900 in which the spacer 904 has been bent outward (away from the patient) at its ends to rotate the entire left and right pillow assemblies 902a, 902b outward. FIG. 11B shows another exemplary horizontal bend setting of the patient ventilation interface 900 in which the spacer 904 has been bent inward (toward the patient) at its ends to rotate the entire left and right pillow assemblies 902a, 902b inward. Such horizontal bending capability of the spacer 904 may be more readily implemented by the inclusion of a preformed U-shaped or V-shaped bend 905 in the spacer 904 at a midpoint between the left and right pillow assemblies 902a, 902b as shown in FIG. 11. As the preformed bend 905 is manually widened (opened) or narrowed (closed), the spacer 904 may be effectively bent outward or inward, respectively.

FIG. 12 is a top view of the patient ventilation interface 900 showing a stretch capability of the spacer 904. By manually pulling apart the left and right pillow assemblies 902a, 902b to shrink the preformed bend 905, the patient may effectively stretch or lengthen the spacer 904, causing the nasal pillows 910 to sit farther from each other (e.g. to match the distance between the patient's nostrils). FIG. 12A shows an exemplary stretch setting of the patient ventilation interface 900 in which the spacer 904 has been extended to its maximum length by the stretch adjustment and the preformed bend 905 has thus been completely eliminated, placing the nasal pillows 910 at their maximum distance from each other. By pushing the left and right pillow assemblies 902a, 902b toward each other again, the preformed bend 905 may be reformed as the spacer 904 again bends to accommodate the adjustment.

FIG. 13 is a perspective view of the patient ventilation interface 900 of FIG. 9 showing a twist capability of the spacer 904. FIG. 13A shows an exemplary twist setting of the patient ventilation interface 900. As can be seen, the spacer 904 may allow the patient ventilation interface 900 to be freely deformed in a variety of ways, such as to have one of the pillow assemblies 902a, 902b facing inward and the other facing outward as shown. By allowing the patient to freely adjust the orientation of each nasal pillow 910 in three dimensions in this way, the spacer 904 may support compatibility of the patient ventilation interface 900 with a wide variety of patient anatomies and preferences to enhance comfort and fit (and thus patient compliance).

Figure 14A:
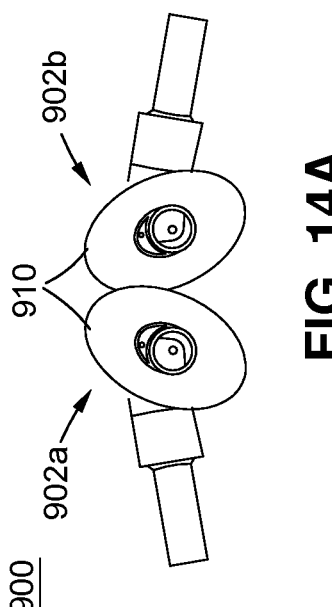
FIG. 14A depicts an exemplary rotational setting of the patient ventilation interface shown in FIG. 9.
Figure 14B:
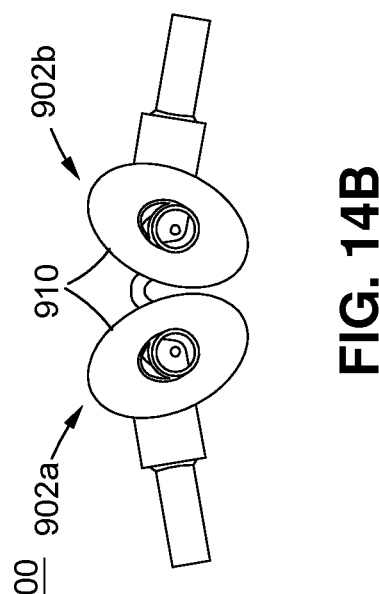
FIG. 14B depicts another exemplary rotational setting of the patient ventilation interface shown in FIG. 9.
Figure 14:
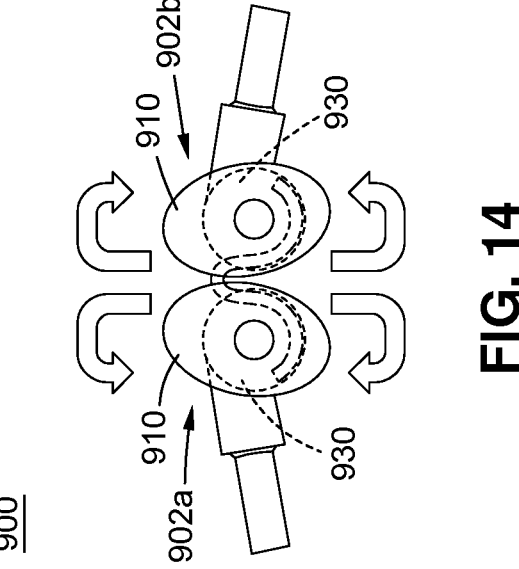
FIG. 14 is a top view of the patient ventilation interface of FIG. 9 showing a rotational capability of a pair of nasal pillows integrated therein.

FIG. 14 is a top view of the patient ventilation interface 900 of FIG. 9 showing a rotational capability of the nasal pillows 910. As noted above, it is contemplated that the nasal pillows 910 may be configured to swivel about their respective throat bodies 930. FIG. 14 illustrates this swivel or rotational capability of the nasal pillows 910. relative to the rest of the respective pillow assemblies 902a, 902b. FIG. 14A shows an exemplary rotational setting of the patient ventilation interface 900 in which the nasal pillows 910 have been rotated oppositely to each other, with the nasal pillow 910 that is aligned with the patient's left nostril being rotated clockwise and the nasal pillow 910 that is aligned with the patient's right nostril being rotated counterclockwise. FIG. 14B shows another exemplary rotation setting of the patient ventilation interface 900 in which the nasal pillows 910 have been rotated oppositely to the rotation setting of FIG. 14A. This time, the nasal pillow 910 that is aligned with the patient's left nostril has been rotated counterclockwise and the nasal pillow 910 that is aligned with the patient's right nostril has been rotated clockwise. The nasal pillows 910 may also be rotatable in the same direction as each other, rather than oppositely. By having rotatable nasal pillows 910 that are non-circular (e.g. elliptical), the patient ventilation interface 900 may be comfortably inserted into a wide variety of nostril anatomies.

As noted above, the nasal pillows 110 may be made of a flexible material such as an elastomer that conforms to the inside of the patient's nostril and creates a seal to prevent leakage between the nasal pillow 110 and the nostril during use. In this regard, the nasal pillows 110, 910 may be made of a thermoplastic elastomer (TPE) or a thermoset produced by liquid injection molding (LIM) using liquid silicone rubber (LSR), for example. The other structures of the patient ventilation interface 100, 800, 900, such as the throat body 130, 930, entry piece 160, ventilation gas tube 170, 870, 970, sheath 180, and housing 990, may be assembled from one or more pieces, which may be attached to each other by ultrasonic welding, for example. These structures may similarly be made of a thermoplastic or thermoset and may typically (though not necessarily) have greater rigidity than the nasal pillows 110, 910 (which may be specifically designed to conform to the patient's nostrils).

The controller 220 of the system 10 (which may be a controller of a ventilator 200 as noted above) may be implemented with a programmable integrated circuit device such as a microcontroller or control processor. Broadly, the device may receive certain inputs, and based upon those inputs, may generate certain outputs. The specific operations that are performed on the inputs may be programmed as instructions that are executed by the control processor. In this regard, the device may include an arithmetic/logic unit (ALU), various registers, and input/output ports. External memory such as EEPROM (electrically erasable/programmable read only memory) may be connected to the device for permanent storage and retrieval of program instructions, and there may also be an internal random-access memory (RAM). Computer programs for implementing any of the disclosed functionality of the controller 220 may reside on such non-transitory program storage media, as well as on removable non-transitory program storage media such as a semiconductor memory (e.g. IC card), for example, in the case of providing an update to an existing device. Examples of program instructions stored on a program storage medium or computer-readable medium may include, in addition to code executable by a processor, state information for execution by programmable circuitry such as a field-programmable gate arrays (FPGA) or programmable logic device (PLD).

Figures 15, 16:
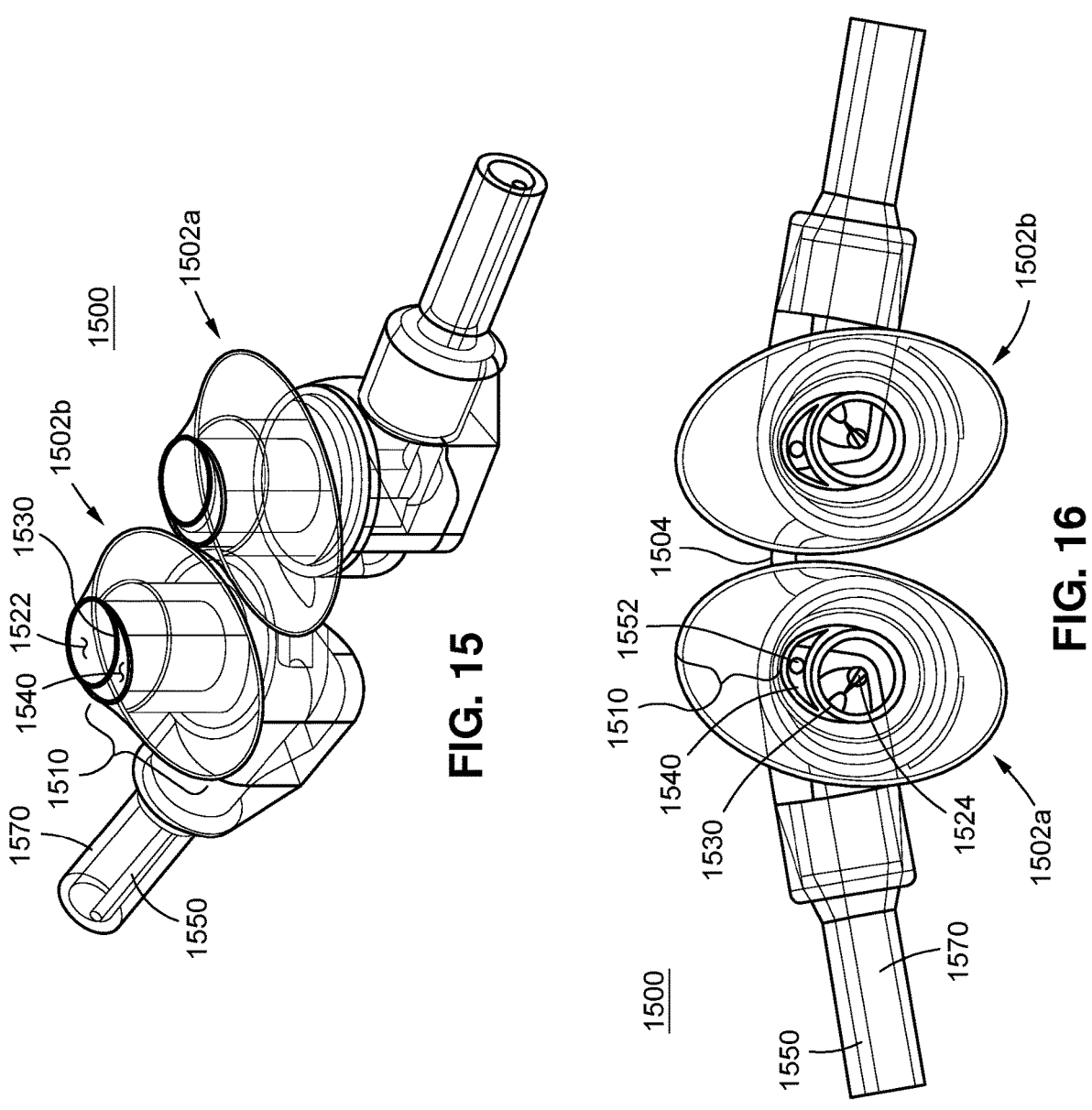
FIG. 15 is a perspective view of another exemplary patient ventilation interface according to an embodiment of the present disclosure.
FIG. 16 is a top view of the patient ventilation interface shown in FIG. 15.
Figure 17:
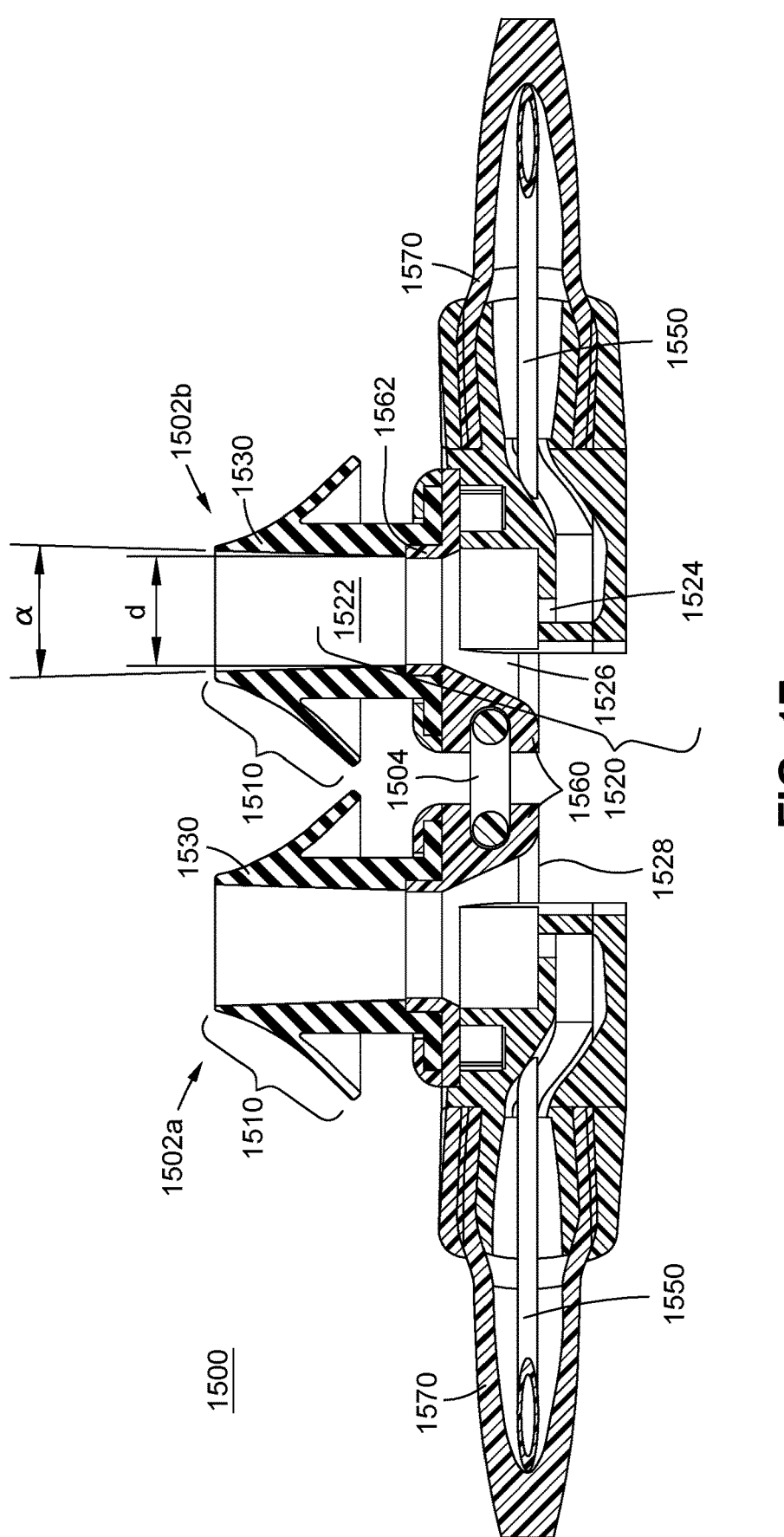
FIG. 17 is a cross-sectional front view of the patient ventilation interface shown in FIG. 15.

FIG. 15 is a perspective view of another exemplary patient ventilation interface 1500 according to an embodiment of the present disclosure. FIGS. 16 and 17 are top and cross-sectional side views of the patient ventilation interface 1500, respectively. The patient ventilation interface 1500 may likewise be integrated into a system 10 such as the exemplary non-invasive ventilation system 10 including the ventilator 200 and multi-lumen tubing 300 shown in FIG. 5, except that the patient ventilation interface 1500 shows another alternative form factor including some additional features, any or all of which may be incorporated into the patient ventilation interfaces 100, 800, 900 described above. For example, whereas each of the patient ventilation interfaces 100, 800, 900 has a pair of nasal pillows 110, 910 that is disposed around a throat body 130, 930 that defines the venturi throat 122, 922, the patient ventilation interface 1500 may instead have a pair of nasal pillow bodies 1530 that each incorporate a nasal pillow portion 1510 as an integral part thereof. In particular, the component of the patient ventilation interface 1500 that defines the venturi throat 1522 may be unitized with the component that is inserted into the patient's nares so as to form a single nasal pillow body 1530. It should be noted that, in some cases, the nasal pillow body 1530 may still be referred to as a throat body, with the nasal pillow portion 1510 thereof referred to simply as a nasal pillow although it may be formed as an integral part of such throat body.

As illustrated, each nasal pillow body 1530 may define a venturi throat 1522 of a corresponding jet venturi 1520, with the venturi throat 1522 being open to ambient air. Each nasal pillow body 1530 may have a nasal pillow portion 1510 that is disposed around the venturi throat 1522 to define a plenum 1540 within the nasal pillow body 1530 and outside the venturi throat 1522. At least the nasal pillow portion 1510 of each nasal pillow body 1530 may be fabricated from the same materials described above in relation to the nasal pillows 110, 910. Two such nasal pillow bodies 1530 may be provided respectively for left and right pillow assemblies 1502a, 1502b, which may be functionally the same as the nasal pillows 110 of the left and right pillow assemblies 102a, 102b shown in FIGS. 1-5 and 8. The left and right pillow assemblies 1502a, 1502b may be spaced part by a spacer 1504 that may be the same as the spacer 104 or spacer 904, for example. The nasal pillow bodies 1530, and in particular the nasal pillow portions 1510 thereof, may have elliptical rather than circular cross-sections, similar to the nasal pillows 910 of FIG. 9, in order to better accommodate the anatomical shape of the patient's nostrils for a more comfortable fit and a better seal. Of particular note, the plenum 1540 defined within the nasal pillow body 1530 and outside the venturi throat 1522 may advantageously have a crescent-shaped cross-section as shown in FIGS. 15 and 16. In comparison with an annular plenum 140, 940 as described above (see, e.g., FIGS. 1, 2, and 9), the crescent-shaped cross-section of the plenum 1540 may allow for a smaller cross-section of the nasal pillow bodies 1530 where they enter the patient's nose (as the crescent-shaped plenum 1540 need only protrude on one side of the nasal pillow body 1530, allowing the nasal pillow body 1530 elsewhere to be only as large as necessary to define the venturi throat 1522). Moreover, the construction of the nasal pillow portion 1510 (that fits in the nostril) as an integrally formed part of the nasal pillow body 1530 (that defines the venturi throat 1522) may use less material and simplify manufacturing by allowing them to be made in a single molding process without later assembly.

In order to sense the pressure within the crescent-shaped plenum 1540, the patient ventilation interface 1500 may include, in each pillow assembly 1502a, 1502b (or in some cases only in one of them), a pressure sensing tube 1550 having a distal pressure sensing port 1552 positioned to be in fluid communication with the crescent-shaped plenum 1540 just like the pressure sensing port 152 of the pressure sensing tube 150 described in relation to the patient ventilation interface 100. A portion of the pressure sensing tube 1550 may likewise be disposed within a respective ventilation gas tube 1570 that terminates in the jet nozzle 1524 and may be the same as the ventilation gas tube(s) 170, 870, 970 described above. For example, the pressure sensing tube may extend from the ventilation gas tube 1570 into the nasal pillow body 1530 to position the pressure sensing port 1522 in fluid communication with the plenum 1540 (which may be via a pressure sensing passage defined by the nasal pillow body 1530 that may be the same as the pressure sensing passage 114, for example).

As best illustrated in FIG. 17, the venturi throat 1522 may taper outwardly away from the jet nozzle 1524 so that it is largest where it enters deepest into the patient's nares. In this regard, the nasal pillow body 1530 may be shaped so as to have a gradually increasing internal diameter defining the venturi throat 1522. In the illustrated embodiment, by way of example, the nasal pillow body 1530 is assembled with a flared entry piece 1560 defining a venturi inlet 1526 of the jet venturi 1520. The flared entry piece 1560 meets the nasal pillow body 1530 at the proximal end of the venturi throat 1522 (i.e., nearest the jet nozzle 1524 and farthest from the patient), with the nasal pillow body 1530 fitting over and around an unflared straight portion 1562 of the entry piece 1560. With this construction, the nasal pillow body 1530 may define a diameter d of the venturi throat 1522 at its proximal end that is equal to or nearly equal to the diameter of the unflared portion 1562 of the entry piece 1560. The venturi throat 1522 may thereafter increase in diameter at an opening angle α (see FIG. 17), which may be defined between an axis of the venturi throat 1522 and an interior wall of the nasal pillow body 1530, for example. The opening angle α may be between 0.5 and 30 degrees, preferably between 1 and 10 degrees. By tapering the venturi throat 1522 in this way, the performance of the venturi throat 1522 may be improved in that an expanding throat may recover energy better than does a cylindrical throat. In addition, manufacturability may be improved as a conventional molding process may require a draft angle (e.g., at least 1.5 or 2 degrees), making a true cylindrical throat more difficult (and therefore more expensive) to produce. It should be noted that an outwardly tapering venturi throat 1522 may be especially practical owing to the smaller overall cross-section of the nasal pillow body 1530 that is made possible by the crescent-shaped plenum 1540 described above. As such, the feasibility of an outwardly tapering venturi throat 1522 (and its resultant advantages) may be thought of as another advantage of the crescent-shaped plenum 1540 and/or related unitary construction of the nasal pillow body 1530 described above.

In the patient ventilation interfaces 100, 800, 1500 described herein, the jet nozzle 124, 1524 is shown coaxial with the venturi throat 122, 1522 (and the patient ventilation interface 900 may have a similar arrangement.) It has been found that the greatest performance may be achieved with this coaxial arrangement. However, the disclosure is not intended to be so limited. For example, the jet nozzles 124, 1524 may instead be offset from being coaxial with the venturi throat 122, 1522. Introducing such an offset may advantageously reduce the noise of the patient ventilation interface 100, 800, 900, 1500, though also potentially resulting in slightly decreased performance.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A patient ventilation interface comprising:
a throat body defining a venturi throat that is open to ambient air;
a nasal pillow disposed around the venturi throat to define a plenum between the venturi throat and the nasal pillow;
a jet nozzle arranged to output ventilation gas into the venturi throat; and
a pressure sensing tube having a pressure sensing port positioned to be in fluid communication with the plenum.

2. The patient ventilation interface of claim 1, wherein the nasal pillow is an integral part of the throat body.

3. The patient ventilation interface of claim 1, wherein throat body has greater rigidity than the nasal pillow.

4. The patient ventilation interface of claim 1, wherein the plenum has a crescent-shaped cross-section.

5. The patient ventilation interface of claim 1, wherein the venturi throat tapers outwardly away from the jet nozzle.

6. The patient ventilation interface of claim 1, further comprising a ventilation gas tube terminating in the jet nozzle, wherein at least a part of the pressure sensing tube is disposed within the ventilation gas tube.

7. The patient ventilation interface of claim 6, wherein the pressure sensing tube extends from the ventilation gas tube into the throat body to position the pressure sensing port in fluid communication with the plenum.

8. The patient ventilation interface of claim 7, wherein the pressure sensing port of the pressure sensing tube is in fluid communication with the plenum via a pressure sensing passage defined by the throat body.

9. The patient ventilation interface of claim 1, further comprising an entry piece defining a venturi inlet that is in fluid communication with the venturi throat, wherein the jet nozzle is arranged to output the ventilation gas into the venturi throat via the venturi inlet.

10. The patient ventilation interface of claim 9, wherein the entry piece defines one or more entrainment openings by which the venturi throat is open to ambient air.

11. The patient ventilation interface of claim 10, wherein the jet nozzle is arranged to output the ventilation gas into the venturi inlet via an entrainment opening from among the one or more entrainment openings.

12. The patient ventilation interface of claim 11, wherein the venturi inlet flares outward relative to the venturi throat.

13. A non-invasive ventilation system comprising:
the patient ventilation interface of claim 1; and
a pressure sensor fluidly coupled to the pressure sensing tube.

14. The non-invasive ventilation system of claim 13, further comprising a controller programmed to control delivery of the ventilation gas output by the jet nozzle in response to a patient airway pressure $P_{sense}$ sensed by the pressure sensor.

15. The non-invasive ventilation system of claim 14, wherein the controller is programmed to correct for an expected error in the sensed patient airway pressure $P_{sense}$.

16. The non-invasive ventilation system of claim 15, wherein the controller is programmed to correct for the expected error by applying a correction factor $P_{delta}$ indexed by the sensed patient airway pressure $P_{sense}$.

17. The non-invasive ventilation system of claim 16, wherein the correction factor $P_{delta}$ is further indexed by a jet nozzle flow $V'_n$ of the jet nozzle.

18. The non-invasive ventilation system of claim 13, further comprising a non-transitory program storage medium on which are stored instructions, executable by a processor or a programable circuit, to correct for an expected error in the sensed patient airway pressure $P_{sense}$.

19. The non-invasive ventilation system of claim 18, wherein the instructions are executable by the processor or the programmable circuit to correct for the expected error by applying a correction factor $P_{delta}$ indexed by the sensed patient airway pressure $P_{sense}$.

20. The non-invasive ventilation system of claim 19, wherein the correction factor $P_{delta}$ is further indexed by a jet nozzle flow $V'_n$ of the jet nozzle.

21. A method of correcting a sensed patient airway pressure $P_{sense}$ in a patient ventilation interface, the method comprising:
providing a patient ventilation interface including a throat body defining a venturi throat that is open to ambient air, a nasal pillow disposed around the venturi throat to define a plenum between the venturi throat and the nasal pillow, and a jet nozzle arranged to output ventilation gas into the venturi throat;
sensing a patient airway pressure $P_{sense}$ in a pressure sensing tube having a pressure sensing port positioned to be in fluid communication with the plenum; and
correcting for an expected error in the sensed patient airway pressure $P_{sense}$ by applying a correction factor $P_{delta}$ indexed by the sensed patient airway pressure $P_{sense}$.

22. The method of claim 21, wherein the nasal pillow is an integral part of the throat body.

23. A method of non-invasive ventilation, the method comprising:
providing a patient ventilation interface including a throat body defining a venturi throat that is open to ambient air, a nasal pillow disposed around the venturi throat to define a plenum between the venturi throat and the nasal pillow, and a jet nozzle arranged to output ventilation gas into the venturi throat;
sensing a patient airway pressure $P_{sense}$ in a pressure sensing tube having a pressure sensing port positioned to be in fluid communication with the plenum; and
controlling delivery of the ventilation gas output by the jet nozzle in response to a patient airway pressure $P_{sense}$ sensed by the pressure sensor.

24. The method of claim 23, wherein the nasal pillow is an integral part of the throat body.

* * * * *